US012712050B2

(12) United States Patent
Zeng et al.

(10) Patent No.: US 12,712,050 B2
(45) Date of Patent: Aug. 18, 2026

(54) CHROMOSOMAL AND SUB-CHROMOSOMAL COPY NUMBER VARIATION DETECTION

(71) Applicant: Laboratory Corporation of America Holdings, Burlington, NC (US)

(72) Inventors: Qiandong Zeng, Burlington, NC (US); Winnie Xin, Burlington, NC (US); Neil Russell, Burlington, NC (US); Chen Xu, San Diego, CA (US); Kenneth Phillips, Burlington, NC (US)

(73) Assignee: Laboratory Corporation of America Holdings, Burlington, NC (US)

( * ) Notice: Subject to any disclaimer, the term of this patent is extended or adjusted under 35 U.S.C. 154(b) by 905 days.

(21) Appl. No.: 17/855,177

(22) Filed: Jun. 30, 2022

(65) Prior Publication Data

US 2023/0005569 A1 Jan. 5, 2023

Related U.S. Application Data

(60) Provisional application No. 63/216,926, filed on Jun. 30, 2021.

(51) Int. Cl.
*G16B 40/30* (2019.01)
*G06N 5/022* (2023.01)
(Continued)

(52) U.S. Cl.
CPC ............. *G16B 20/20* (2019.02); *G06N 5/022* (2013.01); *G16B 20/10* (2019.02); *G16B 40/20* (2019.02)

(58) Field of Classification Search
CPC ........ G16B 20/20; G16B 20/10; G16B 40/20; G06N 5/022
See application file for complete search history.

(56) References Cited

U.S. PATENT DOCUMENTS 11,397,957 B1 * 7/2022 Najmi .............. G06Q 10/06393
11,697,849 B2 7/2023 Deciu et al.
(Continued)

FOREIGN PATENT DOCUMENTS

KR 20200108150 A 9/2020
WO 2012006291 A2 1/2012
(Continued)

OTHER PUBLICATIONS

Glusman et al., "Identification of Copy Number Variants in Whole-Genome Data Using Reference Coverage Profiles", Frontiers in Genetics, vol. 6, No. 45, Feb. 17, 2015, pp. 1-13.
(Continued)

*Primary Examiner* — Brandon S Cole
(74) *Attorney, Agent, or Firm* — Kilpatrick Townsend & Stockton LLP

(57) ABSTRACT

The present disclosure relates to assessment of genetic variation, and in particular to techniques for detection of chromosomal and sub-chromosomal copy number variations. In one aspect, a computer-implemented method is provided for detecting a presence or absence of copy number variation in a target sample. The method includes obtaining sequencing data for a plurality of samples, determining a first normalized coverage for each segment/element in each of the samples according to the sequencing data, determining a second normalized coverage, including a copy number, for each segment/element in each of the samples according to the first normalized coverage, classifying the copy number for each segment/element in a target set in the target sample based on rule-based approaches, machine learning based approaches, or a combination thereof, and outputting a presence or absence of a copy number variation for each segment/element in the target set in the target sample according to the classification.

19 Claims, 21 Drawing Sheets

(51) Int. Cl.

| | |
|---|---|
| ***G16B 20/00*** | (2019.01) |
| ***G16B 20/10*** | (2019.01) |
| ***G16B 20/20*** | (2019.01) |
| ***G16B 30/10*** | (2019.01) |
| ***G16B 40/20*** | (2019.01) |

(56) References Cited

U.S. PATENT DOCUMENTS

| | | | | |
|---|---|---|---|---|
| 2013/0012399 | A1 | 1/2013 | Myers et al. | |
| 2014/0180594 | A1 | 6/2014 | Kim et al. | |
| 2016/0300013 | A1* | 10/2016 | Ashutosh | G16B 20/10 |
| 2017/0220735 | A1* | 8/2017 | Duenwald | G16B 20/20 |
| 2018/0300450 | A1* | 10/2018 | Hogan | G16B 20/10 |
| 2020/0293590 | A1* | 9/2020 | Rebrov | G06N 20/00 |

FOREIGN PATENT DOCUMENTS

| | | | |
|---|---|---|---|
| WO | 2013166517 | A1 | 11/2013 |
| WO | 2018136882 | A1 | 7/2018 |

OTHER PUBLICATIONS

PCT/US2022/035763 , “International Preliminary Report on Patentability”, Jan. 11, 2024, 15 pages.
PCT/US2022/035763 , “International Search Report and the Written Opinion”, Oct. 13, 2022, 19 pages.
Office Action issued in JP2023-580753 dated Jul. 8, 2025, 4 pages.

* cited by examiner

| Reference position | Name | Region | Target Region Position | Ref. Base | Coverage |
|---|---|---|---|---|---|
| 31140066 | DMD | complement(31140016..31140067) | 2 | G | 970 |
| 31140067 | DMD | complement(31140016..31140067) | 1 | A | 970 |
| 31140064 | DMD | complement(31140016..31140067) | 4 | A | 971 |
| 31140065 | DMD | complement(31140016..31140067) | 3 | A | 973 |
| 31140063 | DMD | complement(31140016..31140067) | 5 | A | 974 |
| 31140062 | DMD | complement(31140016..31140067) | 6 | G | 976 |
| 31140061 | DMD | complement(31140016..31140067) | 7 | A | 981 |
| 31140060 | DMD | complement(31140016..31140067) | 8 | G | 984 |
| 31140059 | DMD | complement(31140016..31140067) | 9 | A | 991 |
| 31140058 | DMD | complement(31140016..31140067) | 10 | A | 996 |
| 31140057 | DMD | complement(31140016..31140067) | 11 | A | 999 |
| 31140016 | DMD | complement(31140016..31140067) | 52 | T | 1000 |
| 31140017 | DMD | complement(31140016..31140067) | 51 | G | 1005 |
| 31140018 | DMD | complement(31140016..31140067) | 50 | C | 1005 |
| 31140056 | DMD | complement(31140016..31140067) | 12 | C | 1005 |
| 31140019 | DMD | complement(31140016..31140067) | 49 | C | 1007 |
| 31140055 | DMD | complement(31140016..31140067) | 13 | A | 1010 |
| 31140020 | DMD | complement(31140016..31140067) | 48 | A | 1011 |
| 31140032 | DMD | complement(31140016..31140067) | 36 | C | 1011 |
| 31140047 | DMD | complement(31140016..31140067) | 21 | C | 1011 |
| 31140024 | DMD | complement(31140016..31140067) | 44 | G | 1012 |
| 31140025 | DMD | complement(31140016..31140067) | 43 | G | 1012 |
| 31140026 | DMD | complement(31140016..31140067) | 42 | A | 1012 |
| 31140046 | DMD | complement(31140016..31140067) | 22 | T | 1012 |
| 31140021 | DMD | complement(31140016..31140067) | 47 | T | 1013 |
| 31140022 | DMD | complement(31140016..31140067) | 46 | G | 1013 |
| 31140027 | DMD | complement(31140016..31140067) | 41 | A | 1013 |
| 31140048 | DMD | complement(31140016..31140067) | 20 | C | 1013 |
| 31140049 | DMD | complement(31140016..31140067) | 19 | T | 1013 |
| 31140053 | DMD | complement(31140016..31140067) | 15 | A | 1013 |
| 31140054 | DMD | complement(31140016..31140067) | 14 | A | 1013 |
| 31140023 | DMD | complement(31140016..31140067) | 45 | T | 1014 |
| 31140031 | DMD | complement(31140016..31140067) | 37 | A | 1014 |
| 31140033 | DMD | complement(31140016..31140067) | 35 | T | 1014 |
| 31140034 | DMD | complement(31140016..31140067) | 34 | T | 1014 |
| 31140052 | DMD | complement(31140016..31140067) | 16 | A | 1014 |
| 31140029 | DMD | complement(31140016..31140067) | 39 | A | 1015 |
| 31140035 | DMD | complement(31140016..31140067) | 33 | C | 1015 |
| 31140039 | DMD | complement(31140016..31140067) | 29 | C | 1015 |
| 31140050 | DMD | complement(31140016..31140067) | 18 | G | 1015 |
| 31140051 | DMD | complement(31140016..31140067) | 17 | G | 1015 |
| 31140028 | DMD | complement(31140016..31140067) | 40 | A | 1016 |
| 31140037 | DMD | complement(31140016..31140067) | 31 | T | 1016 |
| 31140030 | DMD | complement(31140016..31140067) | 38 | G | 1017 |
| 31140038 | DMD | complement(31140016..31140067) | 30 | A | 1017 |
| 31140041 | DMD | complement(31140016..31140067) | 27 | T | 1017 |
| 31140045 | DMD | complement(31140016..31140067) | 23 | G | 1017 |
| 31140036 | DMD | complement(31140016..31140067) | 32 | C | 1018 |

FIG. 2

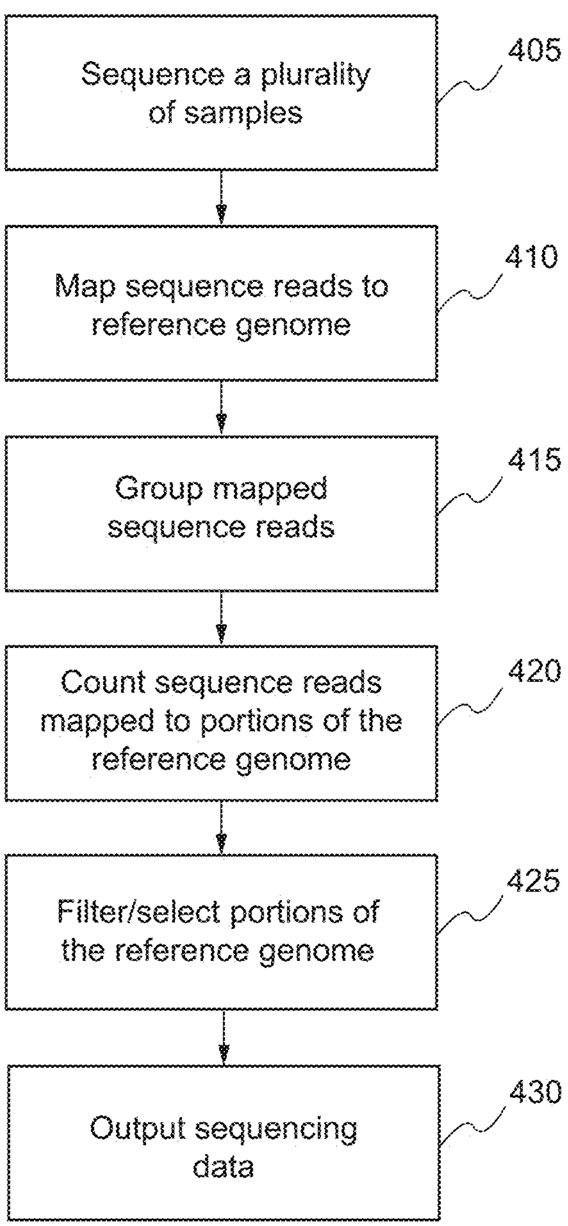
FIG. 4

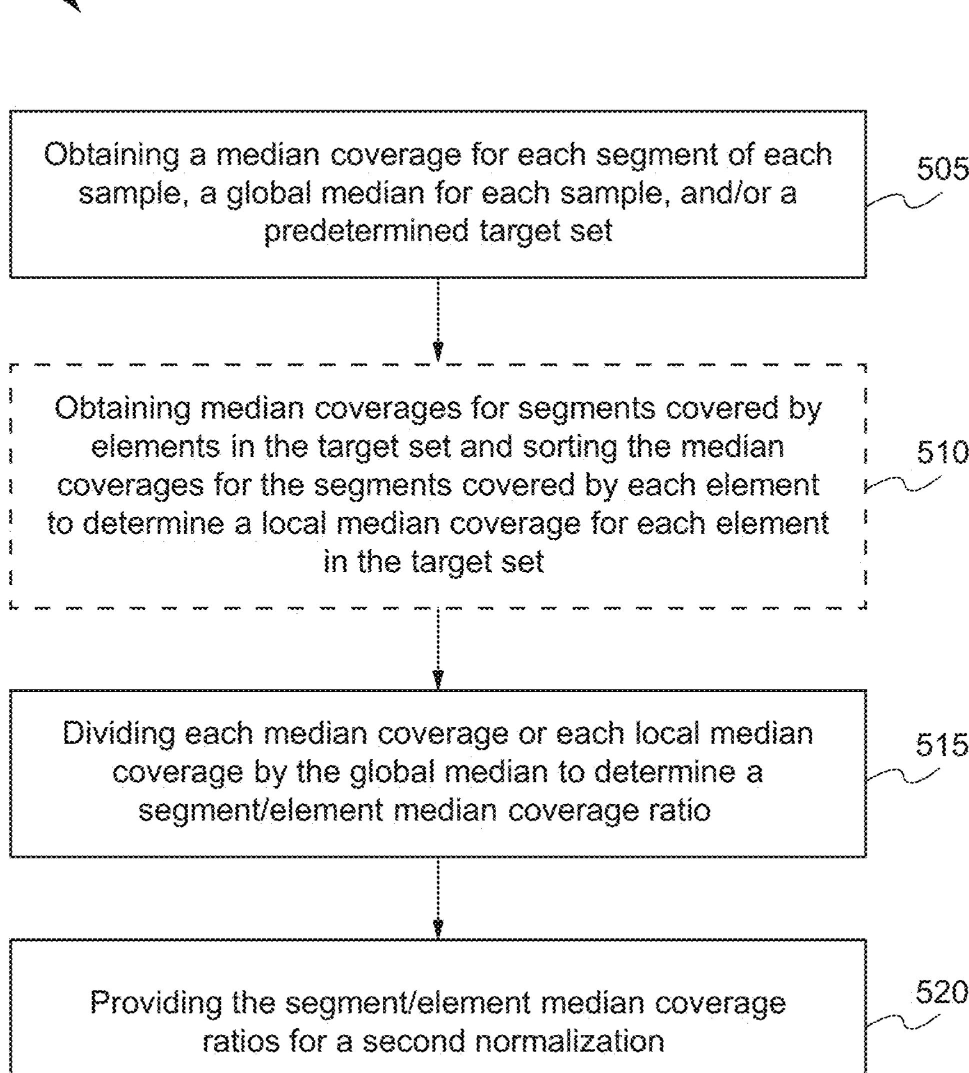
FIG. 5

| Sample 1 | | Segments | | | | | | | | |
|---|---|---|---|---|---|---|---|---|---|---|
| | Median Coverage for the Segment | 1 | 2 | 3 | 4 | 5 | 6 | . . . | (n) | Local Median Coverage for Elements in the Target Set |
| Elements in a Target Set | A | 1064 | 1099 | 1054 | N/A | N/A | N/A | . . . | N/A | 1064 |
| | B | N/A | 1099 | 1054 | 1078 | 1034 | N/A | . . . | N/A | 1066 |
| | C | N/A | N/A | N/A | 1078 | 1034 | N/A | . . . | N/A | 1056 |
| | . . . | . . . | . . . | . . . | . . . | . . . | . . . | . . . | . . . | . . . |
| | (N) | N/A | N/A | N/A | N/A | N/A | 1060 | . . . | 1054 | 1057 |
| | | 1064 | 1099 | 1054 | 1078 | 1034 | 1060 | . . . | 1054 | Global Median for Sample 1 =1060 |

FIG. 9A

| Elements in the Target Set in Sample 1 | Local Median Coverage for the Elements in the Target Set | First Normalized Coverage for Elements in the Target Set |
|---|---|---|
| A | 1064 | 1064/1060=1.0038 |
| B | 1066 | 1066/1060=1.0057 |
| C | 1056 | 1056/1060=0.9962 |
| . . . | . . . | . . . |
| (N) | 1057 | 1057/1060=0.9972 |
| | Global Median for Sample 1 =1060 | |

FIG. 9B

| First Normalized Coverage | Element B | Formula for Determining Second Normalized Coverage | Second Normalized Coverage for Element B |
|---|---|---|---|
| Sample 1 | 1.0057 | 1.0057/1.0656 | 0.9438 |
| Sample 2 | 0.9444 | 0.9444/1.0656 | 0.8863 |
| Sample 3 | 1.0419 | 1.0419/1.0656 | 0.9778 |
| Sample 4 | 0.8931 | 0.8931/1.0656 | 0.8382 |
| Sample 5 | 1.4544 | 1.4543/1.0656 | 1.3649 |
| Sample 6 | 1.1153 | 1.1153/1.0656 | 1.0467 |
| . . . | . . . | . . . | |
| Sample Z | 1.0042 | 1.0042/1.0656 | 0.9424 |
| Mean Coverage | 1.0656 | | |

FIG. 9C

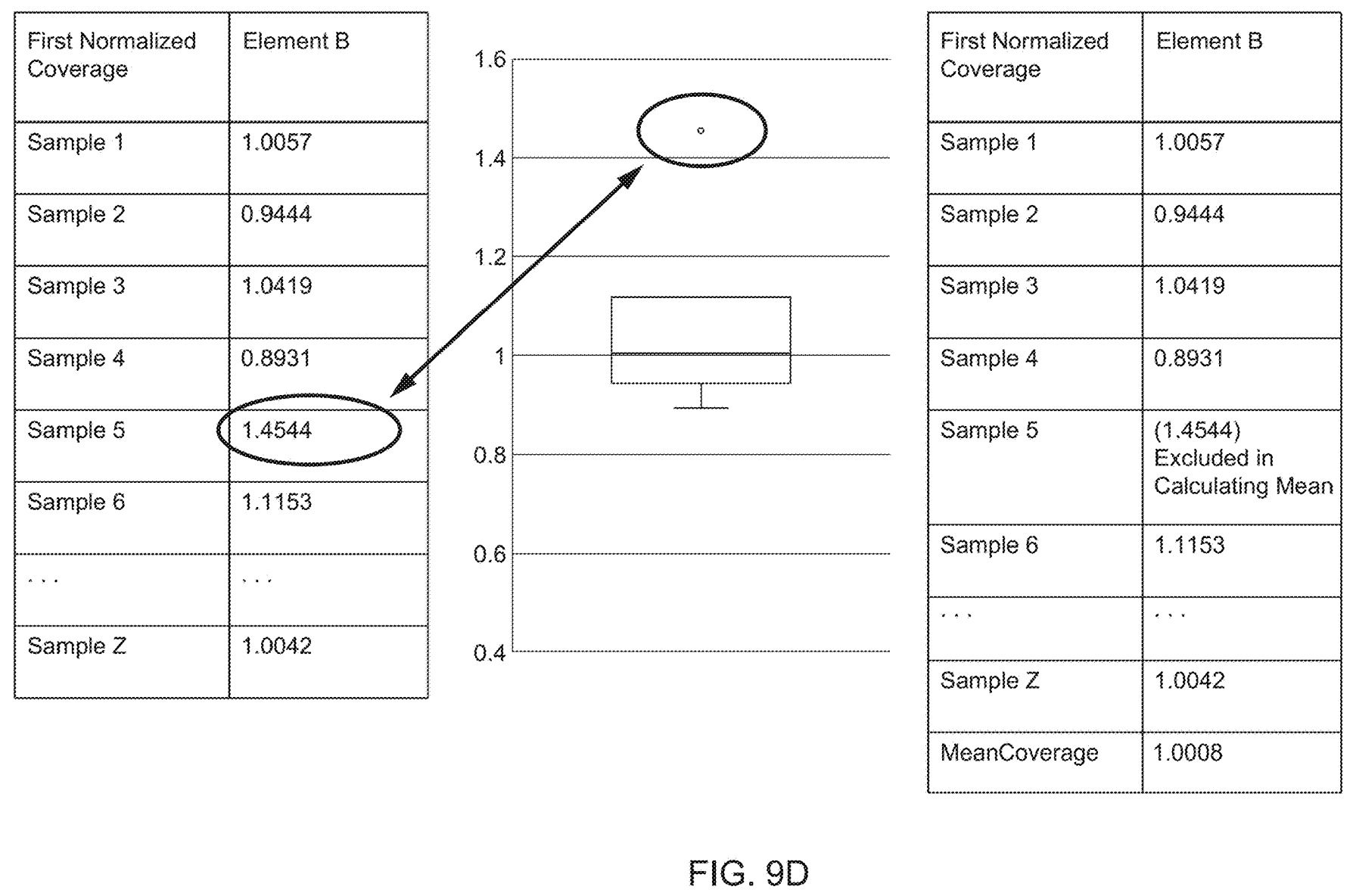

| First Normalized Coverage | Element B |
|---|---|
| Sample 1 | 1.0057 |
| Sample 2 | 0.9444 |
| Sample 3 | 1.0419 |
| Sample 4 | 0.8931 |
| Sample 5 | 1.4544 |
| Sample 6 | 1.1153 |
| . . . | . . . |
| Sample Z | 1.0042 |

1.6
1.4
1.2
1
0.8
0.6
0.4

| First Normalized Coverage | Element B |
|---|---|
| Sample 1 | 1.0057 |
| Sample 2 | 0.9444 |
| Sample 3 | 1.0419 |
| Sample 4 | 0.8931 |
| Sample 5 | (1.4544) Excluded in Calculating Mean |
| Sample 6 | 1.1153 |
| . . . | . . . |
| Sample Z | 1.0042 |
| MeanCoverage | 1.0008 |

FIG. 9D

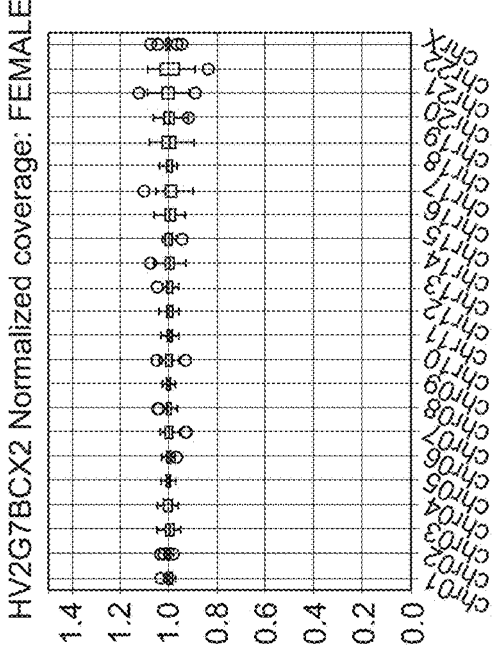
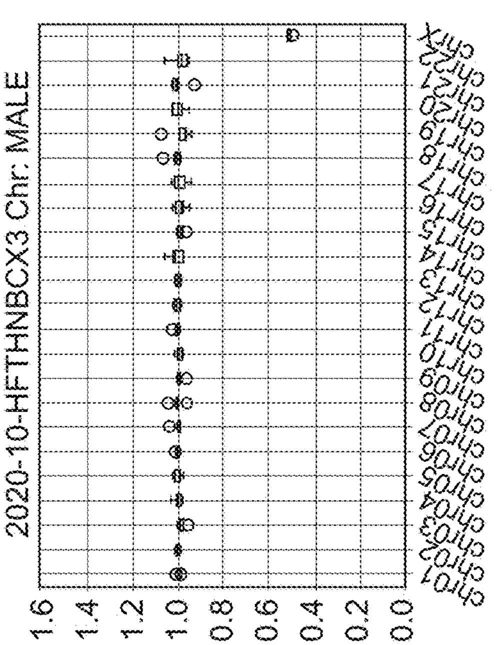
FIG. 12B
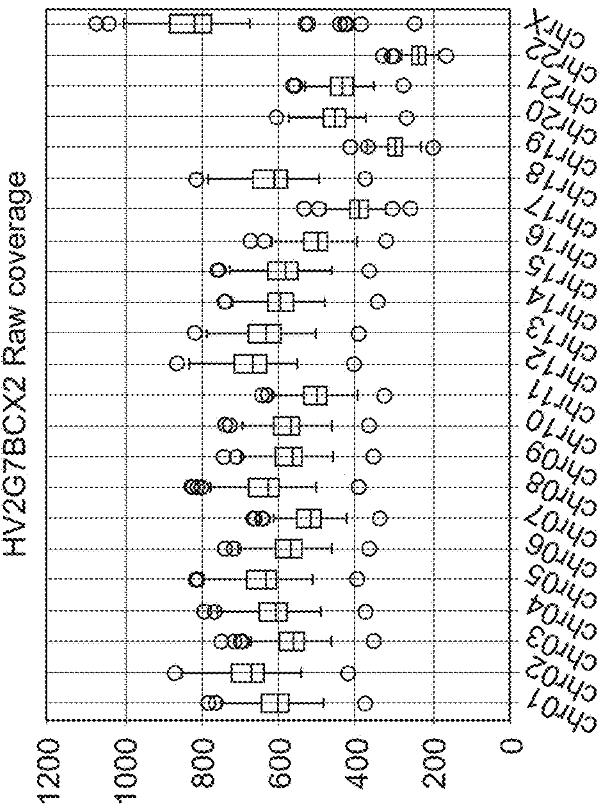
FIG. 12A

FIG. 14
2020-09-HFTHNBCX3 chrX Genes: FEMALE
1.6
1.2
1.0
0.8
0.6
0.4
PDHA1
DMD
OTC
IL2RG
IDS
21.1
q21.1
Xq23
24
Xq25
Xq28

| sample | gender | gen | exon | media | zscor | pvalue | cnv_typ | flowcel | tru | GC_pc | raw_ | cnv_type_ne | cnvty | RF_pre | concor | catego | pvalue_log10 |
|---|---|---|---|---|---|---|---|---|---|---|---|---|---|---|---|---|---|
| 64169129 | FEMALE | GALC | GALC-X11 | 0.7772 | -1.7837 | 0.01165 | pvalue_fil | HNT5JBCX | Y | 0.307692 | 265.5 | pvalue_filt | DEL | DEL | disagree | FN | -1.933674075 |
| 64169129 | FEMALE | GALC | GALC-X12 | 0.6701 | -3.2873 | 3.34E-06 | cnvdel | HNT5JBCX | Y | 0.322835 | 261 | pvalue_filt | DEL | DEL | disagree | FN | -5.476773958 |
| 64169129 | FEMALE | GALC | GALC-X15 | 0.6358 | -6.1567 | 3.12E-18 | cnvdel | HNT5JBCX | Y | 0.367647 | 371 | pvalue_filt | DEL | DEL | disagree | FN | -17.50542802 |
| 64169472 | FEMALE | DMD | DMD-X78 | 0.686 | -4.8443 | 7.34E-12 | cnvdel | HNT5TBCX | Y | 0.416667 | 345 | pvalue_filt | DEL | DEL | disagree | FN | -11.13436311 |
| 64184596 | FEMALE | GALT | GALT-X08 | 0.6273 | -4.7212 | 2.44E-11 | cnvdel | HNNJVBCX | Y | 0.578035 | 370 | pvalue_filt | DEL | DEL | disagree | FN | -10.61225434 |
| 64182733 | FEMALE | GALT | GALT-X08 | 0.7179 | -4.267 | 1.60E-09 | cnvdel | HNNKVBCX | Y | 0.578035 | 366 | pvalue_filt | DEL | DEL | disagree | FN | -8.796967113 |
| 64181676 | FEMALE | GALT | GALT-X02 | 0.6197 | -5.4285 | 1.63E-14 | cnvdel | HNNTFBCX | Y | 0.619048 | 150 | pvalue_filt | DEL | DEL | disagree | FN | -13.7883456 |
| 64181676 | FEMALE | GALT | GALT-X08 | 0.8221 | -2.3485 | 0.000896 | pvalue_fil | HNNTFBCX | Y | 0.578035 | 495 | pvalue_filt | DEL | DEL | disagree | FN | -3.04769199 |
| 64194022 | MALE | GALT | GALT-X08 | 0.7227 | -4.1474 | 4.48E-09 | cnvdel | HNT2JBCX | Y | 0.578035 | 440 | pvalue_filt | DEL | DEL | disagree | FN | -8.348528148 |

FIG. 17B

CHROMOSOMAL AND SUB-CHROMOSOMAL COPY NUMBER VARIATION DETECTION

CROSS-REFERENCE TO RELATED APPLICATIONS

This application claims the benefit of and priority to U.S. Provisional Patent Application No. 63/216,926, filed Jun. 30, 2021, which is incorporated herein by reference in its entirety for all purposes.

FIELD

The present disclosure relates to assessment of genetic variation, and in particular to techniques for detection of chromosomal and sub-chromosomal copy number variation.

BACKGROUND

Genetic information of living organisms is encoded in deoxyribonucleic acid (DNA) or ribonucleic acid (RNA). The genetic information is a succession of nucleotides or modified nucleotides representing the primary structure of chemical or hypothetical nucleic acids. In humans, there are about 25,000 protein-coding genes and over ten thousand non-coding genes, which fulfills specific biochemical or regulatory functions within a living cell.

Many medical conditions are caused by variation in the genetic information of living organism (e.g., genetic variation). For example, certain genetic disorders cause medical conditions such as Duchenne Muscular Dystrophy (DMD). These genetic disorders can result from a mutation (addition, substitution, or deletion) of one or more nucleotides in a particular gene, a mutation in multiple genes, or changes in the number or structure of chromosomes. Certain birth defects are also caused by a chromosomal abnormality, also referred to as an aneuploidy, such as Trisomy 21 (Down's Syndrome), Monosomy X (Turner's Syndrome), and certain sex chromosome aneuploidies such as Klinefelter's Syndrome (XXY).

Identifying genetic variation (e.g., copy number alterations/aberrations (CNAs), copy number variations (CNVs), single nucleotide variations, chromosome alterations, translocations, deletions, insertions, and the like) or variance, can lead to diagnosis of, or determining predisposition to, a particular medical condition, as well as facilitating a medical decision and employing a helpful medical procedure. Next-generation sequencing (NGS) is a modern technique that has enabled genome-wide characterization of genetic variation. NGS refers to a process of massively parallel sequencing that produces a large number of target sequence reads. Genome-wide characterization of genetic variation such as CNVs typically begins with the alignment of sequence reads to a reference sequence. In paired-end sequencing, the alignment process yields three smaller datasets: (1) reads mapped with "correct" pairing, with expected orientation and distance between mates, (2) reads mapped in pairs deemed "discordant" in terms of distance and/or orientation, or where only one read is mapped, and (3) reads that are not mapped at all. A read pair or a single read can map to a single location on the reference sequence ("uniquely mapped") or to multiple different locations ("non-uniquely mapped"), depending on the sequence of the read or the read pair and the contents of the reference sequence. Once all possible reads have been mapped, the resulting read depth serves as a quantitative measure of genome-wide copy number. Segmentation algorithms and other methods have been developed to call variants such as CNVs from the read depth.

SUMMARY

Disclosed are methods, systems, and computer readable storage media for detection of chromosomal and sub-chromosomal copy number variations. The methods, systems, and computer readable storage media may be embodied in a variety of ways.

In various embodiments, a computer-implemented method for detecting a presence or absence of copy number variation in a target sample is provided comprising: obtaining, by a computing device, sequencing data for a plurality of samples in a batch, including the target sample, where one or more of the samples are from different subjects, and where the sequencing data comprises, for each of the samples: (i) a median coverage for each segment in a sample, and (ii) a global median coverage for all segments in the sample; determining, by the computing device, a first normalized coverage for each segment in each of the samples, where the determining the first normalized coverage comprises determining a segment median coverage ratio for a segment in a sample based on the median coverage for the segment and the global median coverage for all segments in the sample; determining, by the computing device, a second normalized coverage for each segment in each of the samples, where the determining the second normalized coverage comprises determining a copy number for a segment in a sample based on the segment median coverage ratio for the segment in the sample and a mean of the segment median coverage ratio for the segment in all of the samples in the batch; comparing, by the computing device, the copy number for each segment in a target set in the target sample to a predetermined interval, where the target set comprises one or more segments from all of the segments in the target sample; and outputting, by the computing device, a classification for the presence or absence of the copy number variation for each segment in the target set in the target sample according to the comparing.

In some embodiments, the obtaining the sequencing data comprises: sequencing, by a massively parallel sequencer, nucleic acids from each sample, where the sequencing generates sequence reads; mapping the sequence reads to a reference genome; counting the sequence reads mapped to genomic portions of the reference genome, where the counting generates a quantification of the sequence reads mapped to the genomic portions of the reference genome for each sample; determining a base coverage for each reference base within each segment of each sample based on the quantification of the sequence reads mapped to each reference base within each segment; determining the median coverage for each segment in each sample; and determining the global median coverage for all segments in each sample.

In some embodiments, the sequencing of the nucleic acids generates hundreds of thousands to hundreds of millions of the sequence reads for each sample.

In some embodiments, the determining the segment median coverage ratio for the segment in the sample comprises dividing the median coverage for the segment by the global median coverage for all segments in the sample.

In some embodiments, the determining the second normalized coverage for each segment in each of the samples further comprises removing outliers from the median coverage for the segment in each of the samples before determining the mean of the segment median coverage ratio for the segment in all of the samples in the batch, and calculating the mean of the segment median coverage ratio for the segment in remaining samples of the samples in the batch.

In some embodiments, the removing the outliers comprises: calculating an interquartile range based on the segment median coverage ratio for the segment in all of the samples in the batch; determining an upper limit and a lower limit relating to the interquartile range; and removing any segment median coverage ratio for the segment where a value of the segment median coverage ratio is greater than the upper limit or less than the lower limit.

In some embodiments, the determining the copy number for the segment in the sample comprises dividing the segment median coverage ratio for the segment by the mean of the segment median coverage ratio for the segment in all of the samples in the batch.

In some embodiments, the computer-implemented method further comprises (i) removing one or more median coverage for one or more segments on a sex chromosome in one or more samples from the obtained sequencing data, (ii) removing one or more median coverage for one or more segments on Chromosome X in one or more samples associated with male subjects from the obtained sequencing data, (iii) doubling one or more median coverage for one or more segments on Chromosome X in one or more samples associated with male subjects in the obtained sequencing data, or (iv) any combination thereof.

In some embodiments, the determining the segment median coverage ratio for a segment in a sample further comprises doubling each of the segment median coverage ratios for the segments on Chromosome X in each of the samples associated with male subjects.

In some embodiments, the computer-implemented method further comprises: determining, by the computing device, the first normalized coverage for an element in each of the samples, the determining the first normalized coverage for the element comprises: determining a local median coverage for the element in a sample; and determining an element median coverage ratio for the element in the sample based on the local median coverage for the element and the global median coverage for all segments in the sample; determining, by the computing device, the second normalized coverage for the element in each of the samples, the determining the second normalized coverage for the element comprises determining a copy number for the element in a sample based on the element median coverage ratio for the element in the sample and a mean of the element median coverage ratio for the element in all of the samples in the batch; comparing, by the computing device, the copy number for the element in the target sample to a predetermined interval; and outputting, by the computing device, a classification for the presence or absence of the copy number variation for the element in the target sample according to the comparing.

In some embodiments, the element is (i) a chromosome, (ii) a portion of a chromosome, (iii) a gene, (iv) an exon, (v) an intron, or (vi) a predetermined genomic part or region of interest.

In some embodiments, the determining the second normalized coverage for the element further comprises removing outliers from the element median coverage ratio for the element in all of the samples in the batch before determining the mean of the element median coverage ratio for the element in all of the samples in the batch, and calculating the mean of the element median coverage ratio for the element in remaining samples of the samples in the batch.

In some embodiments, the removing the outliers comprises: calculating an interquartile range based on the element median coverage ratio for the element in all of the samples in the batch; determining an upper limit and a lower limit relating to the interquartile range; and removing any element median coverage ratio for the element where a value of the element median coverage ratio is greater than the upper limit or less than the lower limit.

In some embodiments, the computer-implemented method further comprises determining, by the computing device, whether the copy number for each segment in the target set in the target sample is within or outside of the predetermined interval based on the comparing, where the outputting comprises reporting each segment in the target set in the target sample that has a copy number outside the predetermined interval as having the copy number variation, and reporting each segment in the target set in the target sample that has a copy number within the predetermined interval as being normal or not having the copy number variation.

In some embodiments, the computer-implemented method further comprises determining, by the computing device, whether the copy number for the element in the target sample is within or outside of the predetermined interval based on the comparing, where the outputting comprises reporting the element as having the copy number variation when the element in the target sample has a copy number outside the predetermined interval, or reporting the element as being normal or not having the copy number variation when the element in the target sample has a copy number within the predetermined interval.

In some embodiments, the computer-implemented method further comprises: calculating a statistical measure for each segment in the target set and/or the element, where the calculation of the statistical measure is based on a normal profile comprising the copy number for each segment in the target set and/or the element in all samples; and comparing the statistical measure with a predetermined upper-threshold or with a predetermined lower-threshold set for segments and/or the element, where each segment in the target in the target sample that has a copy number within the predetermined interval is only reported as having the copy number variation when the statistical measure of the segment in the target set is greater than the predetermined upper-threshold or less than the predetermined lower-threshold based on the comparing; and/or where the element in the target sample that has a copy number within the predetermined interval is only reported as having the copy number variation when the statistical measure of the element is greater than the predetermined upper-threshold or less than the predetermined lower-threshold based on the comparing.

In some embodiments, the statistical measure comprises (i) a z-score, (ii) a p-value, or (iii) a coefficient of variation.

In some embodiments, the computer-implemented method further comprises inputting, by the computing device, the copy number for each segment in the target set in the target sample and the normal profile into a machine learning model; and classifying, using the machine learning model, the copy number for each segment in the target set in the target sample as indicative of a presence or absence of the copy number variation, where the outputting the classification for the presence or absence of the copy number variation for each segment in the target set in the target sample is performed according to the comparing, the classifying by the machine learning model, or a combination thereof.

In some embodiments, the computer-implemented method further comprises determining a diagnosis of a subject associated with the target sample, where the diagnosis is determined based on the classification for the presence or absence of the copy number variation for each segment in the target set in the target sample and/or the element in the target sample.

In some embodiments, the computer-implemented method further comprises administering a treatment to the subject based on (i) the classification for the presence or absence of the copy number variation for each segment in the target set in the target sample and/or the element in the target sample, and/or (ii) the diagnosis of the subject.

In various embodiments, a computer-implemented method for detecting a presence or absence of copy number variation in a target sample is provided comprising: obtaining, by a computing device, sequencing data for a plurality of samples in a batch, including the target sample, where one or more of the samples are from different subjects, and where the sequencing data comprises, for each of the samples: (i) a median coverage for each segment in a sample, and (ii) a global median coverage for all segments in the sample; determining, by the computing device, a first normalized coverage for an element in each of the samples, the determining the first normalized coverage for the element comprises: determining a local median coverage for the element in a sample; and determining an element median coverage ratio for the element in the sample based on the local median coverage for the element and the global median coverage for all segments in the sample; determining, by the computing device, a second normalized coverage for the element in in each of the samples, the determining the second normalized coverage for the element comprises determining a copy number for the element in a sample based on the element median coverage ratio for the element in the sample and a mean of the element median coverage ratio for the element in all of the samples in the batch; comparing, by the computing device, the copy number for the element in a target sample to a predetermined interval; and outputting, by the computing device, a classification for the presence or absence of the copy number variation for the element in the target sample according to the comparing.

In some embodiments, the element is (i) a chromosome, (ii) a portion of a chromosome, (iii) a gene, (iv) an exon, (v) an intron, or (vi) a predetermined genomic part or region of interest.

In some embodiments, the obtaining the sequencing data comprises: sequencing, by a massively parallel sequencer, nucleic acids from each sample, where the sequencing generates sequence reads; mapping the sequence reads to a reference genome; counting the sequence reads mapped to genomic portions of the reference genome, where the counting generates a quantification of the sequence reads mapped to the genomic portions of the reference genome for each sample; determining a base coverage for each reference base within each segment of each sample based on the quantification of the sequence reads mapped to each reference base within each segment; determining the median coverage for each segment in each; and determining the global median coverage for all segments in each sample.

In some embodiments, the sequencing of the nucleic acids generates hundreds of thousands to hundreds of millions of the sequence reads for each sample.

In some embodiments, the determining the element median coverage ratio for the element in the sample comprises dividing the local median coverage for the element by the global median coverage for all segments in the sample.

In some embodiments, the computer-implemented method further comprises (i) removing one or more median coverage for one or more segments on a sex chromosome in one or more samples from the obtained sequencing data, (ii) removing one or more median coverage for one or more segments on Chromosome X in one or more samples associated with male subjects from the obtained sequencing data, (iii) doubling one or more median coverage for one or more segments on Chromosome X in one or more samples associated with male subjects in the obtained sequencing data, or (iv) any combination thereof.

In some embodiments, the determining the second normalized coverage for the element further comprises removing outliers from the element median coverage ratio for the element in all of the samples in the batch before determining the mean of the element median coverage ratio for the element in all of the samples in the batch, and calculating the mean of the element median coverage ratio for the element in remaining samples of the samples in the batch.

In some embodiments, the removing the outliers comprises: calculating an interquartile range based on the element median coverage ratio for the element in all of the samples in the batch; determining an upper limit and a lower limit relating to the interquartile range; and removing any element median coverage ratio for the element where a value of the element median coverage ratio is greater than the upper limit or less than the lower limit.

In some embodiments, the determining the copy number for the element in the sample comprises dividing the element median coverage ratio for the element by the mean of the element median coverage ratio for the element in all of the samples in the batch.

In some embodiments, the computer-implemented method further comprises determining, by the computing device, whether the copy number for the element in the target sample is within or outside of the predetermined interval based on the comparing, where the outputting comprises reporting the element as having the copy number variation when the element in the target sample has a copy number outside the predetermined interval, or reporting the element as being normal or not having the copy number variation when the element in the target sample has a copy number within the predetermined interval.

In some embodiments, the computer-implemented method further comprises: calculating a statistical measure for the element in the target sample, where the calculation of the statistical measure is based on a normal profile comprising the copy number for the element in all samples; and comparing the statistical measure with a predetermined upper-threshold or with a predetermined lower-threshold set for the element, where the element in the target sample that has a copy number outside the predetermined interval is only reported as having the copy number variation when the statistical measure of the element is greater than the predetermined upper-threshold or less than the predetermined lower-threshold based on the comparing.

In some embodiments, the statistical measure comprises (i) a z-score, (ii) a p-value, or (iii) a coefficient of variation.

In some embodiments, the computer-implemented method further comprises determining a diagnosis of a subject associated with the target sample, where the diagnosis is deter-mined based on the classification for the presence or absence of the copy number variation for the element in the target sample.

In some embodiments, the computer-implemented method further comprises administering a treatment to the subject based on (i) the classification for the presence or absence of the copy number variation for the element in the target sample, and/or (ii) the diagnosis of the subject.

In some embodiments, the computer-implemented method further comprises inputting, by the computing device, the copy number for the element in the target sample and the normal profile into a machine learning model; and classifying, using the machine learning model, the copy number for the element as indicative of a presence or absence of the copy number variation, where the outputting the classification for the presence or absence of the copy number variation for the element is performed according to the comparing, the classifying by the machine learning model, or a combination thereof.

In various embodiments, a computer-implemented method for detecting a presence or absence of copy number variation in a target sample is provided comprising: obtaining, by a computing device, sequencing data for a plurality of samples, including the target sample, wherein one or more of the samples are from different subjects, and wherein the sequencing data comprises, for each of the samples: (i) a statistical coverage for each segment in a sample, and (ii) a global statistical coverage for all segments in the sample; determining, by the computing device, a first normalized coverage for each segment in each of the samples, wherein the determining the first normalized coverage comprises determining a segment statistical coverage ratio for a segment in a sample based on the statistical coverage for the segment and the global statistical coverage for all segments in the sample; determining, by the computing device, a second normalized coverage for each segment in each of the samples, wherein the determining the second normalized coverage comprises determining a copy number for a segment in a sample based on the segment statistical coverage ratio for the segment in the sample and a measure of central tendency of the segment statistical coverage ratio for the segment in all of the samples; inputting, by the computing device, the copy number for each segment in the target set in the target sample and the normal profile into a machine learning model; classifying, using the machine learning model, the copy number for each segment in the target set in the target sample as indicative of a presence or absence of the copy number variation; and outputting, by the computing device, a classification for the presence or absence of the copy number variation for each segment in the target set in the target sample according to the classifying by the machine learning model.

In some embodiments, a non-transitory computer readable storage medium is provided comprising computer program instruction that, when executed by a computer processor, cause the computer processor to perform actions or operations of part or all of one or more methods disclosed herein.

In some embodiments, a computer system is provided comprising a processor and a non-transitory memory, the memory comprising computer program instructions that when executed by the processor, cause the processor to perform actions or operations of part or all of one or more methods disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE FIGURES

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

FIG. 2 shows an exemplary interface providing sequence data including a median coverage for a segment according to various embodiments.

FIG. 4 is a flowchart illustrating a process for sequencing a plurality of samples and obtaining sequencing data according to various embodiments.

FIG. 5 is a flowchart illustrating a process for performing a first normalization and obtaining normalized segment (or element) median coverage ratios according to various embodiments.

FIG. 9A shows an exemplary way to determine a local median coverage for an element in a sample and to determine a global median coverage for all segments in the sample according to various embodiments.

FIG. 9B shows an exemplary way to determine an element median coverage ratio according to various embodiments.

FIG. 9C shows an exemplary way to determine a copy number for an element according to various embodiments.

FIG. 9D shows an exemplary way to exclude an outlier from element median coverage ratios and determine a mean of the element median coverage ratios for the element according to various embodiments.

FIG. 12A shows boxplots of median coverage for segments in different chromosomes (Chromosomes 1-22 and Chromosome X) according to various embodiments.

FIG. 12B shows boxplots of copy numbers for segments in different chromosomes (Chromosomes 1-22 and Chromosome X) associated separately with female and male subjects according to various embodiments.

FIG. 17B shows details concerning discrepancies in CNV calling between the rule-based approaches and the machine learning based approaches according to various embodiments.

DETAILED DESCRIPTION

Figure 1:
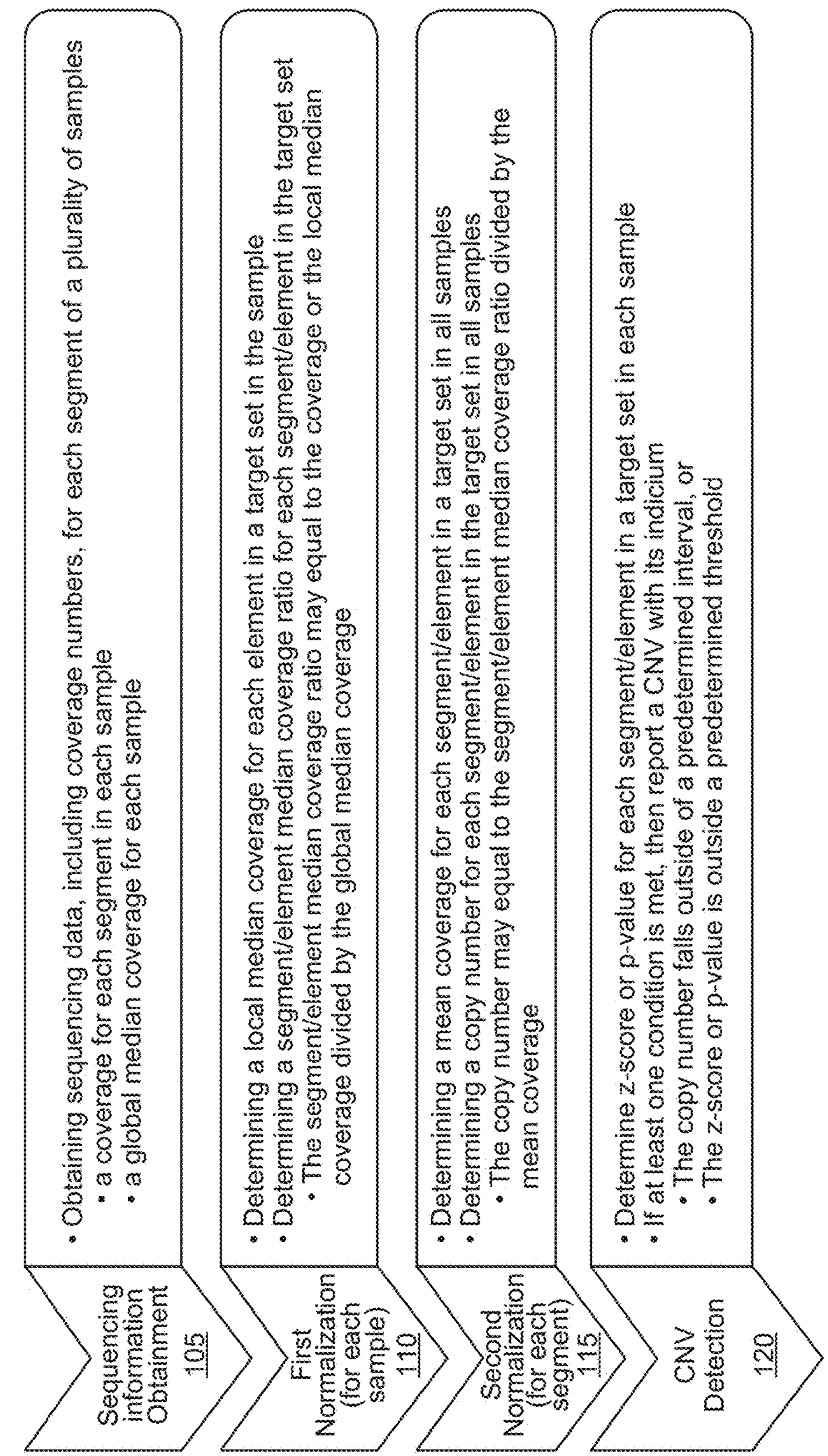
FIG. 1 shows an overview of a process flow for detection of chromosomal and sub-chromosomal copy number variations according to various embodiments.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

I. OVERVIEW

The present disclosure describes techniques for detection of chromosomal and sub-chromosomal copy number variations. More specifically, some embodiments of the present disclosure provide a two-step normalization analysis for detecting and reporting copy number variations without the need for external reference samples.

Copy number variation (CNV) is a prevalent type of genomic disorder (structural genomic variation) that alters chromosomal structure through insertion, duplication, or deletion. When a CNV happens in a human subject, a number of nucleotide base pairs is inserted, duplicated, or deleted in the subject's chromosomes compared to a normal subject. Sometimes multi-insertion, multi-duplication, multi-deletion, or combinations thereof may happen in multiple chromosomes, or a whole or part of chromosome may be duplicated or missing. CNVs are associated with many disease phenotypes and may lead to higher disease risks. For example, patients with Klinefelter Syndrome are males born with an extra X chromosome. Typical symptoms of Klinefelter Syndrome are not obvious and hard to diagnosis: including greater height, lower energy level, and infertility. Klinefelter Syndrome may lead to a higher risk of other health issues such as Type II Diabetes and male breast cancer.

CNV analysis was initially studied by observing the physical structure of the chromosome through inserted fluorescent probes with conventional techniques such as fluorescence in situ hybridization (FISH). With the development of next-generation sequencing (NGS) techniques, scientists and professional practitioners are able to simultaneously and rapidly detect and analyse targeted structural variants using sequence reads. Massively parallel sequencing data can be used to infer CNVs throughout relevant genomic regions (e.g., hundreds to thousands of genomic regions) of the genome in patient samples. Most traditional sequencing-based approaches for CNV detection partition the genome into nonoverlapping bins and use the read depth (RD) to look for regions that differ in copy number. To accurately detect CNVs, the RD approach requires at least five external samples (ideally around ten) that will be run as a cohort with each subject sample analyzed, using the remaining samples as a pool of reference samples. Alternatively, the paired-end (PE) approach identifies CNV based upon the distances between the paired reads. A genomic aberration is detected when the distance between reads is significantly different from the predetermined insert size. Although it is possible to detect CNV using the PE approach, the method is most often used to detect structural variation such as inversions and translocations. A third approach is based upon assembly of short reads into contigs and excludes mapping of reads to a reference genome. To identify CNV assembled contigs are then compared to a reference genome to identify quantitative differences. Both PE and assembly based approaches are limited however in targeted resequencing applications due to targeted regions being discontinuous across the genome. Therefore, all CNV detection tools for targeted resequencing and whole exome sequencing (WES) are based on the RD approach. Importantly, read depth approaches assume that reads distribute in a more or less uniform way across the genome and, therefore, the differences in read depth for the cohort are used to identify CNVs.

However, this assumption fails in the context of whole genome and targeted sequencing. One of the main reasons for the failure is that the probes used for capturing the different genomic target regions have variable specificity and efficiency depending on the region. This fact introduces strong biases in the number of mapped reads per region that hamper the CNV detection. The traditional CNV detection approaches require multiple external reference samples because the approaches use them to control the biases given by the extensive variability in capture efficiency across target areas. Moreover, different regions in chromosomes may require different thresholds in CNV analysis and further demand extensive experimental and computational tuning. Those reference biases affect the sensitivity and specificity of CNV detection, resulting in a high false positive rate in most of the currently available methods. As a result, the traditional CNV detection approaches are available only for a limited number of target genes or catalogue CNVs, and the majority of the traditional CNV detection approaches have no capability of detecting CNVs for small regions (e.g., small exons).

To address the problems and limitations in the traditional CNV detection approaches, techniques are disclosed herein for detection of chromosomal and sub-chromosomal (e.g., gene level and exon level) copy number variations simultaneously. One illustrative embodiment of the present disclosure is directed to a computer-implemented double-normalization method for calling CNVs at different levels of resolution (e.g., chromosomal level, gene level, and exon level) without external reference samples. In some instances, the computer-implemented method is performed as part of pre-analysis before performing diagnosis of diseases. In some instances, the computer-implemented method is performed as part of pre-analysis before performing administration of a treatment to diseases. In other instances, the computer-implemented method is performed as part of post-analysis or adjusted-analysis after performing a traditional NGS-CNV detection analysis. However, as should be understood by one of ordinary skill in the art, the concepts discussed herein are not limited to pre-analysis, post-analysis, or adjusted-analysis procedures, but may also be integrated into the overall clinical impact of CNV analysis in accordance with various embodiments.

FIG. 1 shows a computer-implemented double-normalization method 100 for calling CNVs (e.g., SMN1 copy number, GAA exon 18 deletion, and the like) at different levels of resolution comprises a two-step normalizing process. At block 105, a batch of samples (e.g., 96 subject samples to be analyzed for CNVs) is preprocessed and sequenced using NGS techniques (this process is explained in further detail with respect to FIG. 4). A set of target genomic regions comprising one or more elements (e.g., chromosome, gene, exon, intron or other region of interest (ROI) such as a segment) is identified to detect certain types of CNVs. In some instances, each element in the set of target genomic regions is a gene, a chromosome, a portion of a chromosome, an exon, an intron, a predetermined genomic portion or ROI such as a segment, or any combination thereof. A median coverage number for each segment in each of the samples is obtained based on preprocessing and sequencing results. A segment is a part of an element such as a chromosome, gene, exon, intron or other ROI. As shown in FIG. 2, a segment median coverage 205 is determined by sorting the coverage values and picking the coverage at the central position in the sorted list. The global median coverage for each sample is determined based on a sorting result of the median coverage numbers for all segments in the sample. It should be pointed out that other measures for a central tendency in a numerical data set or other statistical coverages such as mean coverage and mode coverage could also be used in place of median coverage for the segments and/or the global median coverage to obtain similar results with similar performance in many cases. However, compared with mean coverage, the median coverage is generally more robust and much less affected by extreme values.

When samples associated with subjects of different genders are processed together, an adjustment may be required before proceeding with a first normalization. Because each sample associated with a male subject has only one Chromosome X, a median coverage for a segment on Chromosome X in a sample associated with a male subject should be doubled and updated before determining a global median coverage for the sample. In various embodiments, a doubling of a median coverage for a segment in a sample associated with a male subject is processed and the corresponding original median coverage is updated for further processing. In some embodiments, a doubling of a median coverage for a segment in a sample associated with a male subject is stored as a new variable for the segment for further processing. In other embodiments, a median coverage for a segment on a sex chromosome in a sample associated with a male subject is removed before determining a global median coverage for the sample. It should be appreciated that a median coverage for an element on Chromosome X in a sample associated with a male subject may be adjusted in a similar way as above. Alternatively, the median coverage for an element on Chromosome X in a sample associated with a male subject may be adjusted on the fly, by applying the 2× doubling factor to the male samples before analyzing male and female samples together. It should also be appreciated that the adjustment may be only for determining a global median coverage and a subsequent adjustment may be processed after a first normalization.

With reference back to FIG. 1, at block 110, a first normalization is performed where each sample is processed independently (this process is explained in further detail with respect to FIG. 5). The input is the median coverage for all segments of each sample. It is assumed that the segment median coverage follows a normal distribution. The coverage for each segment is normalized ("scaling towards the global median") by dividing each segment median coverage by the sample or global median coverage—this is the normalized segment median coverage ratio for each segment. The same normalization may be performed for each sample on an element by element basis to obtain different levels of resolution. For example, normalization for each additional element (e.g., a gene or chromosome) may comprise: (a) similar to obtaining individual segment median coverage, but only consider segments belonging to that element, to find the element median coverage for that element as opposed to all the segments of the whole sample; and (b) divide each element median coverage by the sample or global median coverage—this is the normalized element median coverage ratio for each additional element.

When samples associated with subjects of different genders are processed together, an adjustment may be required when proceeding with the first normalization. Because each sample associated with a male subject has only one Chromosome X, if a median coverage for a segment on Chromosome X in a sample associated with a male subject is not doubled for the first normalization, a segment median coverage ratio for the segment on Chromosome X in the sample associated with the male subject should be doubled and updated before determining the segment median coverage ratio for a second normalization. In various embodiments, a doubling of a segment median coverage ratio for a segment in a sample associated with a male subject is processed and the corresponding original segment median coverage ratio is updated for further processing. In some embodiments, a doubling of a segment median coverage ratio for a segment in a sample associated with a male subject is stored as a new variable for the segment for further processing. It should be appreciated that an element median coverage ratio for an element on Chromosome X in a sample associated with a male subject may be adjusted in a similar way as above.

Figure 6:
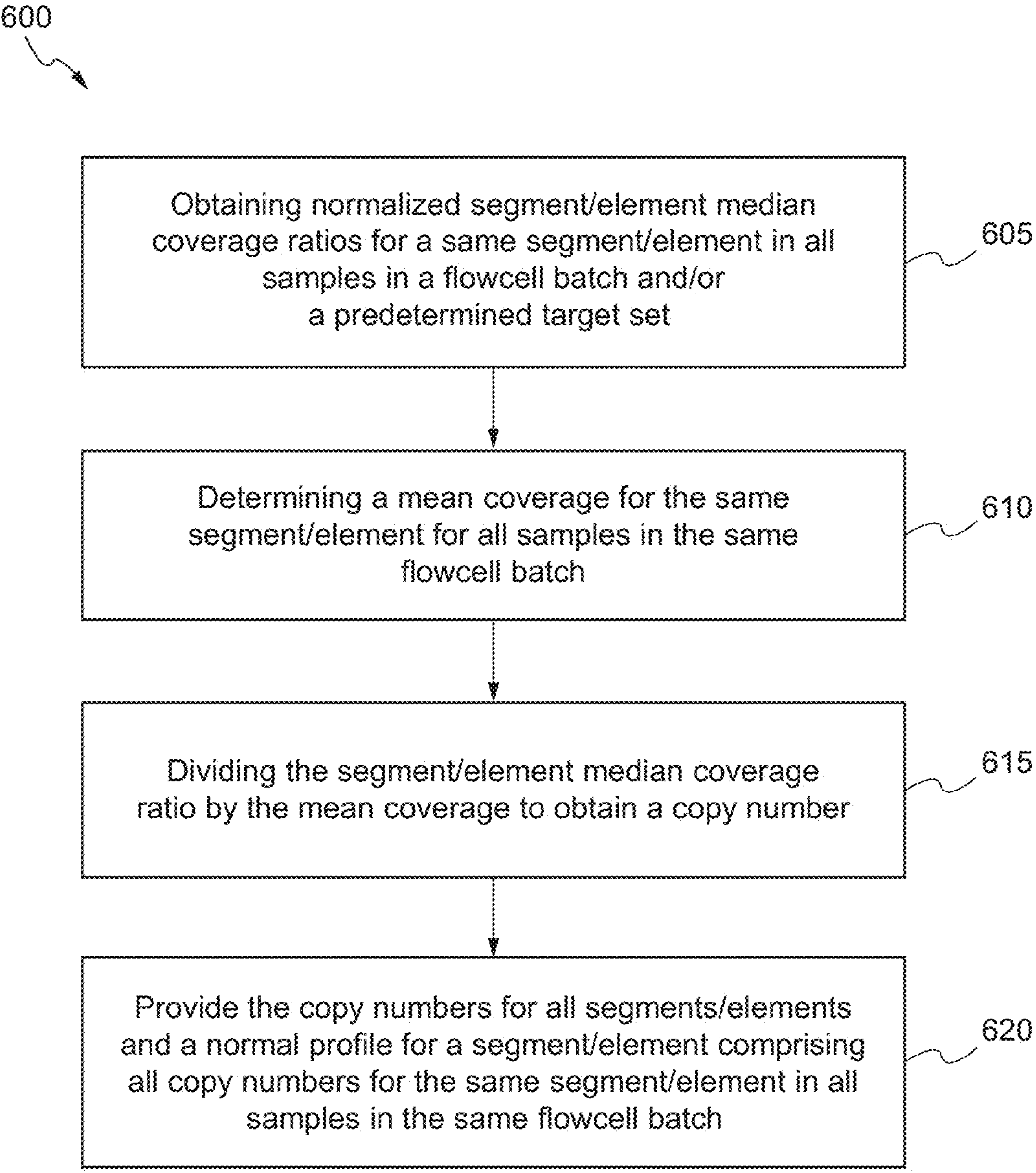
FIG. 6 is a flowchart illustrating a process for performing a second normalization and obtaining copy number coverages according to various embodiments.

At block 115, a second normalization is performed where all samples within a batch (e.g., a flowcell batch) of samples are processed jointly (this process is explained in further detail with respect to FIG. 6). The input is the first normalized coverage for the segments/elements. It is assumed that most samples in a batch have normal copy numbers for the segments/elements to be analyzed. This assumption may not hold for a few rare cases, e.g., HBA analysis, where up to thirty percent of samples may have copy number variations. In such rare cases, the present method should not be used for copy number analysis. This input can be used to build a simple model of normal copy numbers of segments (or elements) and the model is then used to detect segments (or elements) with significantly different copy numbers. Each segment (or element) in all samples is considered an independent analysis unit. In the unit, a batch mean coverage is determined by adding all first normalized coverage for the segments (or elements) in all samples and dividing the sum by the number of samples. In some embodiments, outliers to the unit may be excluded before determining the mean coverage (an exemplary outlier exclusion is illustrated in FIG. 8D). Outlier detection may be an important step to remove any potential CNVs and anomalous segments to obtain a reliable statistic profile model for the normal samples. After outlier filtering, the second normalized coverage for the segment (or element) in each sample is determined by dividing a sample segment (or element) median coverage ratio by the flowcell mean for each sample. In other words, the coverage per segment (or element) is being normalized by dividing the median coverage ratio of a segment (or element) of a single sample by the mean of median coverage ratio of that particular segment (or gene or chromosome) of all the samples in the flowcell batch. Subsequently or in parallel with the second normalization process, a normal model/profile for the segment (or element) comprising all second normalized coverages for the same segment (or element) in all samples is determined and prepared to be used in CNV detection.

Figure 7:
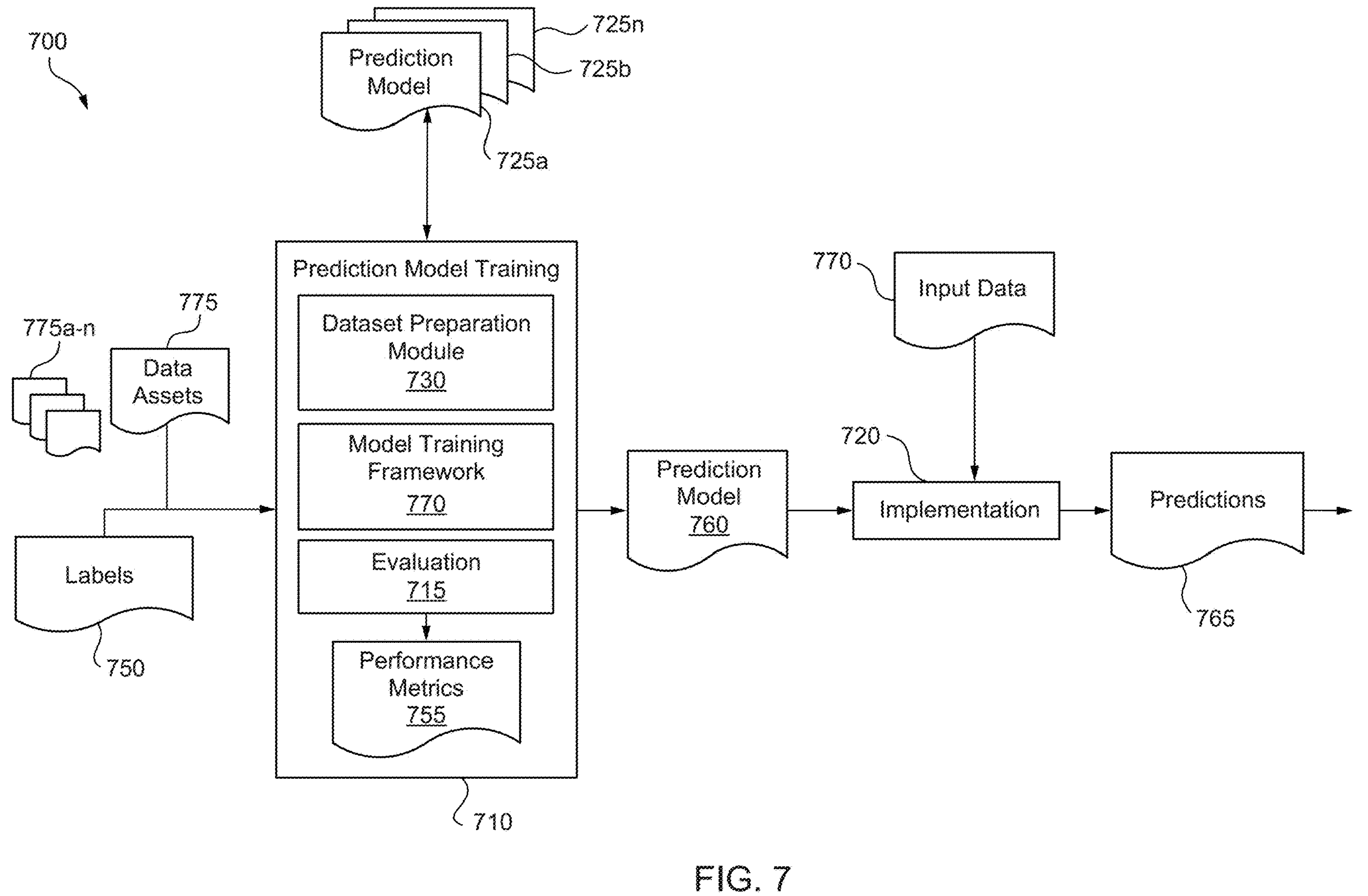
FIG. 7 depicts a block diagram illustrating a machine learning system for training and deploying machine-learning models in accordance with various embodiments.
Figure 8:
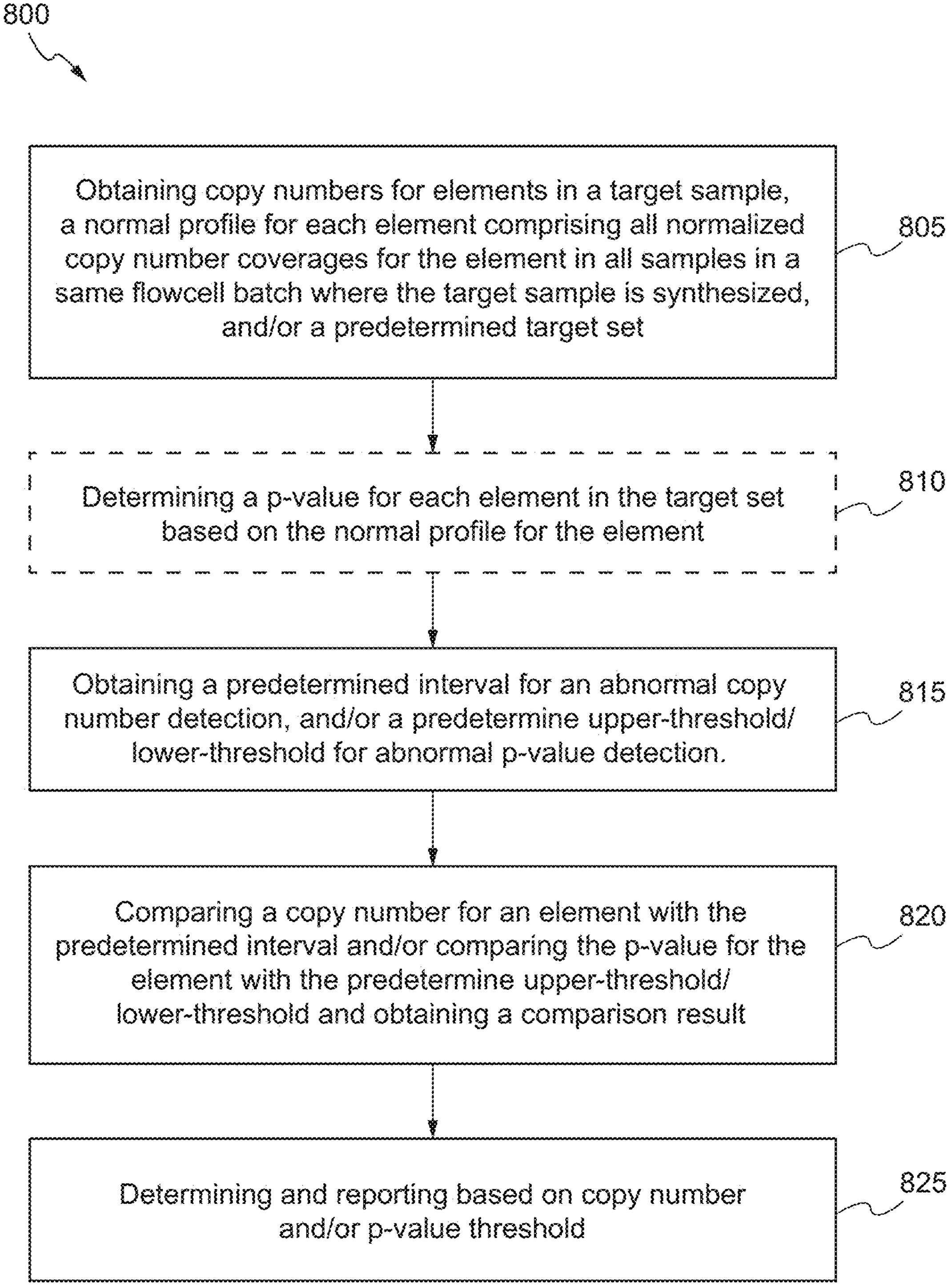
FIG. 8 is a flowchart illustrating a process for performing and reporting a CNV detection according to various embodiments.

At block 120, absence or presence of CNV is detected using artificial intelligence techniques (this process is explained in further detail with respect to FIGS. 7 and 8). The artificial intelligence techniques including rule-based methods, machine learning models, or a combination thereof. CNV detection is based on the results of the second normalization, specifically copy number per segment (or element), or the p-value (or the corresponding z-score, or a statistical measure) for the segment (or element) or both the copy number and the p-value (or the corresponding z-score, or a statistical measure). For example, for each sample-segment (or element) combination, a particular sample may be compared with the model/profile of normal samples for that segment to calculate the z-score and p-value for the segment (or element). In various embodiments, a presence of CNV associated with an element in a target sample is reported based on rule-based methods, for example, when the copy number for the segment (or element) falls out of a predetermined interval and optionally its corresponding z-score and/or p-value is outside a predetermined threshold (s). In other embodiments, a presence of CNV associated with an element in a target sample is reported based on one or more machine learning models, for example, a machine learning model may be used to predict a duplication (i.e., increased copy number) or deletion (i.e., decreased copy number). In yet other embodiments, a presence of CNV associated with an element in a target sample is reported based on a combination of rule-based methods and one or more machine learning models. The reporting information may include but not limited to (i) an ID for the target sample, (ii) an indicium (e.g., name or location) of the segment (or element), (iii) the copy number for the segment (or element), (iv) the p-value (or the corresponding z-score, or a statistical measure) for the segment (or element), (v) gender of a subject associated with the target sample, (vi) gene indicium of the element if the element is an exon/intron, (vii) chromosome indicium of the element if the element is an exon/intron/gene, (viii) a type of the CNV detection (e.g., cnvdup, cnvdel, or the absence of a CNV), or (ix) any combination thereof.

The double-normalizing process is advantageous in many aspects, for example: (i) it is capable of simultaneously detecting CNVs at different resolutions such as chromosomes and sub-chromosomes (e.g., genes and exons), and is especially applicable to detect small regional CNVs such as small-exon CNVs; (ii) it does not demand external "normal" reference samples and eliminates possible biases and errors in adjusting the reference samples (perfectly CNV-normal samples are very rare to find and use as the reference); (iii) it avoids false positives and false negatives caused by artifacts due to batch-to-batch variations and (iv) it provides a series of standard procedures to fast and efficiently detect and analyse CNVs automatically. Moreover, the double-normalizing data process can be easily adapted to other target-based germline NGS tests, and potentially somatic CNV mutation analysis.

II. DEFINITIONS

As used herein, when an action is "based on" something, this means the action is based at least in part on at least a part of the something.

As used herein, the terms "substantially," "approximately," and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

As used herein, the term "sample," "biological sample," "tissue," or "tissue sample" refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain embodiments, the term "biological sample" as used herein refers to a sample (such as a homogenized or liquefied sample) prepared from a tumor or a portion thereof obtained from a subject.

As used herein, the term "portion," "genomic section," "bin," "partition," "portion of a reference genome," "portion of a chromosome" or "genomic portion" refers to a product by partitioning of a genome according to one or more features. Non-limiting examples of certain partitioning features include length (e.g., fixed length, non-fixed length) and other structural features. Genomic portions sometimes include one or more of the following features: fixed length, non-fixed length, random length, non-random length, equal length, unequal length (e.g., at least two of the genomic portions are of unequal length), do not overlap (e.g., the 3' ends of the genomic portions sometimes abut the 5' ends of adjacent genomic portions), overlap (e.g., at least two of the genomic portions overlap), contiguous, consecutive, not contiguous, and not consecutive. Genomic portions sometimes are about 1 to about 1,000 kilobases in length (e.g., about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900 kilobases in length), about 5 to about 500 kilobases in length, about 10 to about 100 kilobases in length, or about 40 to about 60 kilobases in length.

As used herein, the term "segment" or "genomic segment" refers to one or more fixed-length genomic portions, and often includes one or more consecutive fixed-length portions (e.g., about 2 to about 100 such portions (e.g., 2, 3, 4, 5, 6, 7, 8, 9, 10, 11, 12, 13, 14, 15, 16, 17, 18, 19, 20, 25, 30, 35, 40, 45, 50, 60, 70, 80, 90 such portions)). A segment or genomic segment is a part of the target chromosome, gene, exon, intron or other region of interest.

As used herein, the term "element" refers to two or more fixed-length genomic portions, and often includes two or more consecutive fixed-length portions (e.g., about 2 to about 100 such portions (e.g., 2, 3, 4, 5, 6, 7, 8, 9, 10, 11, 12, 13, 14, 15, 16, 17, 18, 19, 20, 25, 30, 35, 40, 45, 50, 60, 70, 80, 90 such portions)). An element may be a gene, a chromosome, a portion of a chromosome, an exon, an intron, a predetermined genomic portion or ROI such as a segment, or any combination thereof.

As used herein, the term "copy number alteration," "copy number variation," or "CNV" refers to a class or type of genetic variation, genetic alteration or chromosomal aberration. In certain instances, "copy number alteration," "copy number variation," or "CNV" may be used to describe a somatic alteration whereby the genome in a subset of cells in a subject contains the alteration (such as, for example, in tumor or cancer cells). In certain instances, "copy number alteration," "copy number variation," or "CNV" may be used to describe a variation inherited from one or both parents (such as, for example, a copy number variation in a fetus). "Copy number alteration," "copy number variation," or "CNV" can be a deletion (e.g., microdeletion), duplication (e.g., a microduplication) or insertion (e.g., a microinsertion). Often, the prefix "micro" as used herein sometimes is a region of nucleic acid less than 5 Mb in length. A "copy number alteration," "copy number variation," or "CNV" can include one or more deletions (e.g., microdeletion), duplications and/or insertions (e.g., a microduplication, microinsertion) of a part of a chromosome or the whole chromosome. In certain embodiments, a duplication comprises an insertion. In certain embodiments, an insertion is a duplication.

As used herein, the term "read" or "sequence read" is a short nucleotide sequence produced by any sequencing process, including NGS, described herein or known in the art.

As used herein, the terms "aligned," "alignment," or "aligning" generally refer to two or more nucleic acid sequences that can be identified as a match (e.g., 100% identity) or partial match.

As used herein, the term "reference genome" can refer to any particular known, sequenced or characterized genome, whether partial or complete, of any organism or virus which may be used to reference identified sequences from a subject.

III. TECHNIQUES FOR CNV DETECTION

CNV detection and analysis play a vital role in characterizing genetic disorders and syndromes. The present automated CNV detection method, without relying on external reference samples, provides a systematic and reliable way to perform standardized CNV detection and is also capable to provide CNV information on smaller genomic regions such as exons.

Described herein is a computer-implemented method incorporating double-normalization and artificially intelligence techniques for automated calling of CNVs at different levels of resolutions. After obtaining sequencing data, median coverage numbers of segments in each sample are used to determine a first normalized coverage for each segment/element based on the median coverage for the segment or a local median coverage for the element, and a global median coverage for all segments in the sample ("within a sample normalization"), and the first normalized coverage of each segment/element is second-normalized based on a mean coverage for the segment/element in all samples ("across samples normalization"). Each element is a chromosome, portion of a chromosome, gene, exon, intron or other region of interest (ROI)) in a set of target genomic regions. A detection of CNVs is based on results of the second normalization using artificial intelligence techniques. The artificial intelligence techniques include rule-based methods, machine learning models, or a combination thereof. The disclosed method has comparable or better performance for automated CNV detection to traditional NGS-CNV methods relying heavily on human intervention and has better performance in detecting small regional CNVs.

III.A. Samples

Provided herein are systems, methods, and computer readable storage media for detection of chromosomal and sub-chromosomal copy number variations. In some embodiments, analyzed DNA materials include nucleic acid in a mixture of nucleic acid fragments. Nucleic acid fragments may be referred to as nucleic acid templates, and the terms may be used interchangeably herein. A mixture of nucleic acids can comprise two or more nucleic acid fragment species having the same or different nucleotide sequences, different fragment lengths, different origins (e.g., genomic origins, fetal vs. maternal origins, cell or tissue origins, cancer vs. non-cancer origin, tumor vs. non-tumor origin, sample origins, subject origins, and the like), or combinations thereof.

Nucleic acids used herein include DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, RNA highly expressed by a fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides.

Nucleic acids utilized in systems, methods, and computer readable storage media described herein often is isolated from a sample obtained from a subject (e.g., a test subject).

A subject can be any living or non-living organism, including but not limited to a human, a non-human animal, a plant, a bacterium, a fungus, a protest or a pathogen. Any human or non-human animal can be selected, and may include, for example, mammal, reptile, avian, amphibian, and fish. A subject may be a male or female (e.g., woman, a pregnant woman). A subject may be any age (e.g., an embryo, a fetus, an infant, a child, an adult). A subject may be a cancer patient, a patient suspected of having cancer, a patient in remission, a patient with a family history of cancer, and/or a subject obtaining a cancer screen. A subject may be a male or female having circulating cell free tumor DNA (ctDNA). A subject may be a pregnant female having maternal and fetal circulating cell-free DNA (ccfDNA).

III.B. Machines, Software and Interfaces

Certain processes and methods described herein (e.g., mapping, counting, normalizing, range setting, adjusting, categorizing and/or determining sequence reads, counts, levels and/or profiles, CNV analysis, and the like) are performed within a computing environment comprising a computer, microprocessor, software, module, other machines such as sequencers, or combinations thereof. The methods described herein typically are computer-implemented methods, and one or more portions or steps of the method are performed by one or more processors (e.g., microprocessors), computers, systems, apparatuses, or machines (e.g., microprocessor-controlled machine). Computers, systems, apparatuses, machines and computer program products suitable for use often include, or are utilized in conjunction with, computer readable storage media. Non-limiting examples of computer readable storage media include memory, hard disk, CD-ROM, flash memory device and the like. Computer readable storage media generally are computer hardware, and often are non-transitory computer-readable storage media. Computer readable storage media are not computer readable transmission media, the latter of which are transmission signals per se.

Figure 3:
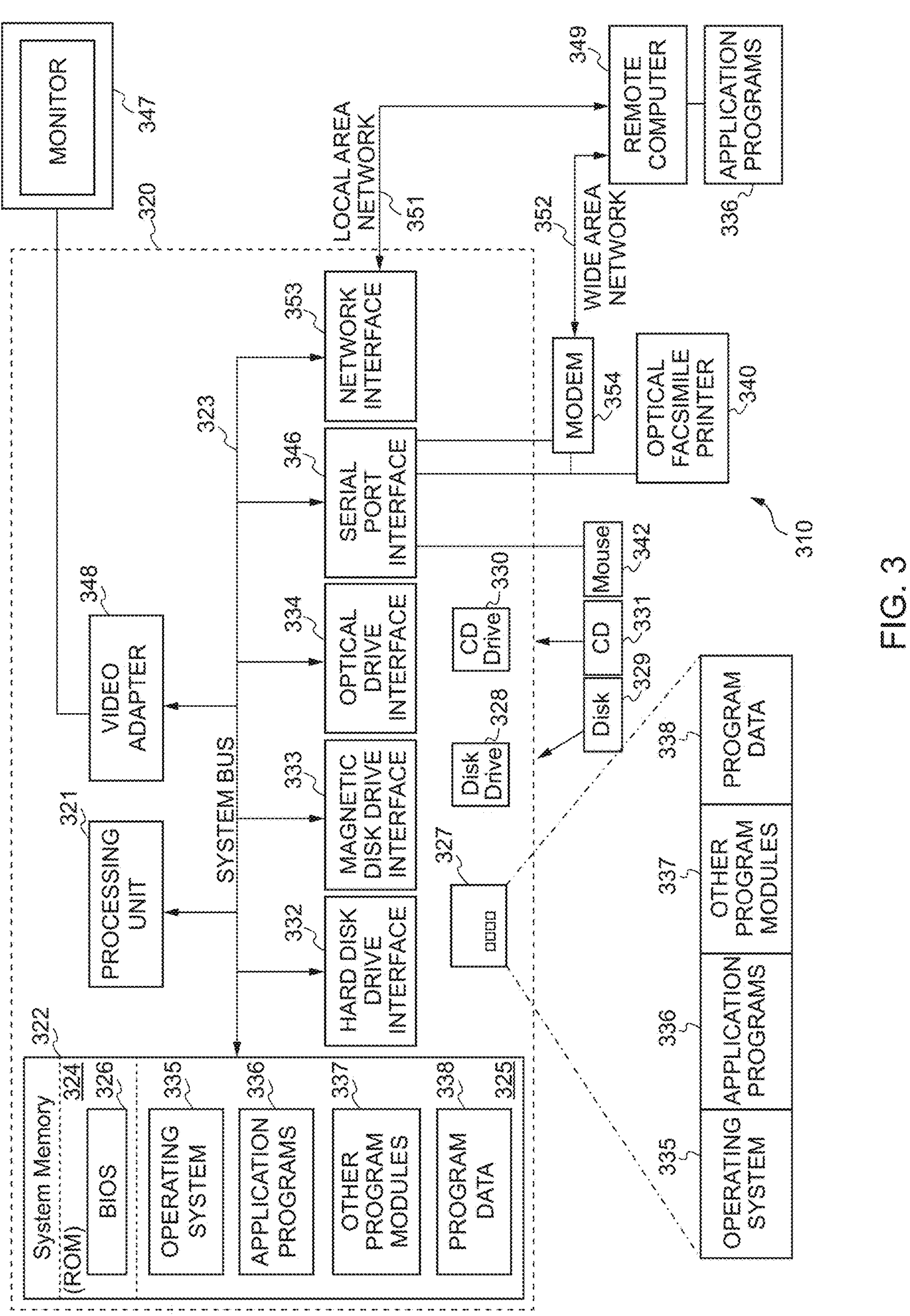
FIG. 3 shows an example of a computing environment to perform the disclosed techniques according to various embodiments.

FIG. 3 illustrates a non-limiting example of a computing environment 310 in which various systems, methods, process, and data structures described herein may be implemented. The computing environment 310 is only one example of a suitable computing environment and is not intended to suggest any limitation as to the scope of use or functionality of the systems, methods, and data structures described herein. Neither should computing environment 310 be interpreted as having any dependency or requirement relating to any one or combination of components illustrated in computing environment 310. A subset of systems, methods, and data structures shown in FIG. 3 can be utilized in certain embodiments. Systems, methods, and data structures described herein are operational with numerous other general purpose or special purpose computing system environments or configurations. Examples of known computing systems, environments, and/or configurations that may be suitable include, but are not limited to, personal computers, server computers, thin clients, thick clients, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The computing environment 310 includes a computing device 320 (e.g., a computer or other type of machines such as sequencers, photo cells, photo multiplier tubes, optical readers, sensors, etc.), including a processing unit 321, a system memory 322, and a system bus 323 that operatively couples various system components including the system memory 322 to the processing unit 321. There may be only one or there may be more than one processing unit 321, such that the processor of computing device 320 includes a single central-processing unit (CPU), or a plurality of processing units, commonly referred to as a parallel processing environment. The computing device 320 may be a conventional computer, a distributed computer, or any other type of computer.

The system bus 323 may be any of several types of bus structures including a memory bus or memory controller, a peripheral bus, and a local bus using any of a variety of bus architectures. The system memory may also be referred to as simply the memory, and includes read only memory (ROM) 324 and random access memory (RAM). A basic input/output system (BIOS) 326, containing the basic routines that help to transfer information between elements within the computing device 320, such as during start-up, is stored in ROM 324. The computing device 320 may further include a hard disk drive interface 327 for reading from and writing to a hard disk, not shown, a magnetic disk drive 328 for reading from or writing to a removable magnetic disk 329, and an optical disk drive 330 for reading from or writing to a removable optical disk 331 such as a CD ROM or other optical media.

The hard disk drive 327, magnetic disk drive 328, and optical disk drive 330 are connected to the system bus 323 by a hard disk drive interface 332, a magnetic disk drive interface 333, and an optical disk drive interface 334, respectively. The drives and their associated computer-readable media provide nonvolatile storage of computer-readable instructions, data structures, program modules and other data for the computing device 320. Any type of computer-readable media that can store data that is accessible by a computer, such as magnetic cassettes, flash memory cards, digital video disks, Bernoulli cartridges, random access memories (RAMs), read only memories (ROMs), and the like, may be used in the operating environment.

A number of program modules may be stored on the hard disk, magnetic disk 329, optical disk 331, ROM 324, or RAM, including an operating system 335, one or more application programs 336, other program modules 337, and program data 338. A user may enter commands and information into the computing device 320 through input devices such as a keyboard 340 and pointing device 342. Other input devices (not shown) may include a microphone, joystick, game pad, satellite dish, scanner, or the like. These and other input devices are often connected to the processing unit 321 through a serial port interface 346 that is coupled to the system bus, but may be connected by other interfaces, such as a parallel port, game port, or a universal serial bus (USB). A monitor 347 or other type of display device is also connected to the system bus 323 via an interface, such as a video adapter 348. In addition to the monitor, computers typically include other peripheral output devices (not shown), such as speakers and printers.

The computing device 320 may operate in a networked environment using logical connections to one or more remote computers, such as remote computer 349. These logical connections may be achieved by a communication device coupled to or a part of the computing device 320, or in other manners. The remote computer 349 may be another computer, a server, a router, a network PC, a client, a peer device or other common network node, and typically includes many or all of the elements described above relative to the computing device 320, although only a memory storage device 350 has been illustrated in FIG. 3.

The logical connections depicted in FIG. 3 include a local-area network (LAN) 351 and a wide-area network (WAN) 352. Such networking environments are commonplace in office networks, enterprise-wide computer networks, intranets and the Internet, which all are types of networks.

When used in a LAN-networking environment, the computing device 320 is connected to the local network 351 through a network interface or adapter 353, which is one type of communications device. When used in a WAN-networking environment, the computing device 320 often includes a modem 354, a type of communications device, or any other type of communications device for establishing communications over the wide area network 352. The modem 354, which may be internal or external, is connected to the system bus 323 via the serial port interface 346. In a networked environment, program modules depicted relative to the computing device 320, or portions thereof, may be stored in the remote memory storage device. It is appreciated that the network connections shown are non-limiting examples and other communications devices for establishing a communications link between computers may be used.

III.C. Sample Sequencing and Obtaining Sequencing Data Including Coverage Numbers FIG. 4 is a flowchart illustrating a process 400 for sequencing a plurality of samples and obtaining sequencing data including coverage numbers according to various embodiments. The processing depicted in FIG. 4 may be implemented in software (e.g., code, instructions, program) executed by one or more processing units (e.g., processors, cores) of the respective systems, hardware, or combinations thereof. The software may be stored on a non-transitory storage medium (e.g., on a memory device). The method presented in FIG. 4 and described below is intended to be illustrative and non-limiting. Although FIG. 4 depicts the various processing steps occurring in a particular sequence or order, this is not intended to be limiting. In certain alternative embodiments, the steps may be performed in some different order or some steps may also be performed in parallel. In certain embodiments, such as in the embodiment depicted in FIG. 3, the processing depicted in FIG. 4 may be performed by a computing device such as a sequencer to generate sequencing data.

At block 405, a plurality of samples are sequenced using a sequencer. The samples are from different subjects and sequenced as a batch run. The samples are all being evaluated for the presence or absence of CNV as part of a clinical laboratory assay, and none of the samples would be considered an external reference sample (i.e., a sample intended solely for purpose or use as a reference sample). The samples include nucleic acid (e.g., nucleic acid fragments, sample nucleic acid, cell-free nucleic acid) that is sequenced to generate a collection of sequence reads (referred to generally herein as "reads"). The sequencing of nucleic acid generates hundreds of thousands to hundreds of millions of sequence reads for each sample. The sequence reads can be generated from one end of nucleic acid fragments ("single-end reads"), or can be generated from both ends of nucleic acid fragments (e.g., paired-end reads, double-end reads).

In some instances, circulating cell free nucleic acid fragments (CCF fragments) obtained from a cancer patient comprise nucleic acid fragments originating from normal cells (i.e., non-cancer fragments) and nucleic acid fragments originating from cancer cells (i.e., cancer fragments). Sequence reads derived from CCF fragments originating from normal cells (i.e., non-cancerous cells) are referred to herein as "non-cancer reads." Sequence reads derived from CCF fragments originating from cancer cells are referred to herein as "cancer reads." CCF fragments from which non-cancer reads are obtained may be referred to herein as non-cancer templates and CCF fragments from which cancer reads are obtained may be referred herein to as cancer templates.

In other instances, circulating cell free nucleic acid fragments (CCF fragments) obtained from a pregnant female comprise nucleic acid fragments originating from fetal cells (i.e., fetal fragments) and nucleic acid fragments originating from maternal cells (i.e., maternal fragments). Sequence reads derived from CCF fragments originating from a fetus are referred to herein as "fetal reads." Sequence reads derived from CCF fragments originating from the genome of a pregnant female (e.g., a mother) bearing a fetus are referred to herein as "maternal reads." CCF fragments from which fetal reads are obtained are referred to herein as fetal templates and CCF fragments from which maternal reads are obtained are referred herein to as maternal templates.

The sequence reads are generally representations of nucleotide sequences in the physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Sequence reads obtained from a sample from a subject can be reads from a mixture of a minority nucleic acid and a majority nucleic acid. For example, sequence reads obtained from the blood of a cancer patient can be reads from a mixture of cancer nucleic acid and non-cancer nucleic acid. In another example, sequence reads obtained from the blood of a pregnant female can be reads from a mixture of fetal nucleic acid and maternal nucleic acid. A mixture of relatively short reads can be transformed by processes described herein into a representation of genomic nucleic acid present in the subject, and/or a representation of genomic nucleic acid present in a tumor or a fetus. In certain instances, a mixture of relatively short reads can be transformed into a representation of a copy number alteration, copy number variation, a genetic variation/genetic alteration, or an aneuploidy, for example. In one example, reads of a mixture of cancer and non-cancer nucleic acid can be transformed into a representation of a composite chromosome or a part thereof comprising features of one or both cancer cell and non-cancer cell chromosomes. In another example, reads of a mixture of maternal and fetal nucleic acid can be transformed into a representation of a composite chromosome or a part thereof comprising features of one or both maternal and fetal chromosomes.

The length of a sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In various embodiments, sequence reads are of a mean, median, average or absolute length of about 150 bp long. In some embodiments, sequence reads are of a mean, median, average or absolute length of about 15 bp to about 900 bp long. In certain embodiments sequence reads are of a mean, median, average or absolute length of about 1000 bp or more. In some embodiments sequence reads are of a mean, median, average or absolute length of about 1500, 2000, 2500, 3000, 3500, 4000, 4500, or 5000 bp or more. In some embodiments, sequence reads are of a mean, median, average or absolute length of about 100 bp to about 200 bp.

Any suitable method of sequencing nucleic acids can be used, non-limiting examples of which include Maxim &

Gilbert, chain-termination methods, sequencing by synthesis, sequencing by ligation, sequencing by mass spectrometry, microscopy-based techniques, the like or combinations thereof. In some embodiments, a first generation technology, such as, for example, Sanger sequencing methods including automated Sanger sequencing methods, including microfluidic Sanger sequencing, can be used in a method provided herein. In some embodiments, sequencing technologies that include the use of nucleic acid imaging technologies (e.g., transmission electron microscopy (TEM) and atomic force microscopy (AFM)), can be used. In some embodiments, a high-throughput sequencing method is used. High-throughput sequencing methods generally involve clonally amplified DNA templates or single DNA molecules that are sequenced in a massively parallel fashion, sometimes within a flow cell. Next generation (e.g., 2nd and 3rd generation) sequencing techniques capable of sequencing DNA in a massively parallel fashion can be used for methods described herein and are collectively referred to herein as "massively parallel sequencing" (MPS). In some embodiments, MPS sequencing methods utilize a targeted approach, where specific chromosomes, genes or regions of interest are sequenced. In certain embodiments, a non-targeted approach is used where most or all nucleic acids in a sample are sequenced, amplified and/or captured randomly.

MPS sequencing sometimes makes use of sequencing by synthesis and certain imaging processes. A nucleic acid sequencing technology that may be used in a method described herein is sequencing-by-synthesis and reversible terminator-based sequencing (e.g., Illumina's Genome Analyzer; Genome Analyzer II; HISEQ 2000; HISEQ 2500 (Illumina, San Diego, CA)). With this technology, millions of nucleic acid (e.g., DNA) fragments can be sequenced in parallel. In one example of this type of sequencing technology, a flow cell is used which contains an optically transparent slide with 8 individual lanes on the surfaces of which are bound oligonucleotide anchors (e.g., adapter primers).

Sequencing by synthesis generally is performed by iteratively adding (e.g., by covalent addition) a nucleotide to a primer or preexisting nucleic acid strand in a template directed manner. Each iterative addition of a nucleotide is detected and the process is repeated multiple times until a sequence of a nucleic acid strand is obtained. The length of a sequence obtained depends, in part, on the number of addition and detection steps that are performed. In some embodiments of sequencing by synthesis, one, two, three or more nucleotides of the same type (e.g., A, G, C or T) are added and detected in a round of nucleotide addition. Nucleotides can be added by any suitable method (e.g., enzymatically or chemically). For example, in some embodiments a polymerase or a ligase adds a nucleotide to a primer or to a preexisting nucleic acid strand in a template directed manner. In some embodiments of sequencing by synthesis, different types of nucleotides, nucleotide analogues and/or identifiers are used. In some embodiments reversible terminators and/or removable (e.g., cleavable) identifiers are used. In some embodiments fluorescent labeled nucleotides and/or nucleotide analogues are used. In certain embodiments sequencing by synthesis comprises a cleavage (e.g., cleavage and removal of an identifier) and/or a washing step. In some embodiments the addition of one or more nucleotides is detected by a suitable method described herein or known in the art, non-limiting examples of which include any suitable imaging apparatus, a suitable camera, a digital camera, a CCD (Charge Couple Device) based imaging apparatus (e.g., a CCD camera), a CMOS (Complementary Metal Oxide Silicon) based imaging apparatus (e.g., a CMOS camera), a photo diode (e.g., a photomultiplier tube), electron microscopy, a field-effect transistor (e.g., a DNA field-effect transistor), an ISFET ion sensor (e.g., a CHEMFET sensor), the like or combinations thereof.

Any suitable MPS method, system or technology platform for conducting methods described herein can be used to obtain nucleic acid sequence reads. Non-limiting examples of MPS platforms include Illumina/Solex/HiSeq (e.g., Illumina's Genome Analyzer; Genome Analyzer II; HISEQ 2000; HISEQ), SOLiD, Roche/454, PACBIO and/or SMRT, Helicos True Single Molecule Sequencing, Ion Torrent and Ion semiconductor-based sequencing (e.g., as developed by Life Technologies), WildFire, 5500, 5500xl W and/or 5500xl W Genetic Analyzer based technologies (e.g., as developed and sold by Life Technologies, U.S. Patent Application Publication No. 2013/0012399); Polony sequencing, Pyrosequencing, Massively Parallel Signature Sequencing (MPSS), RNA polymerase (RNAP) sequencing, LaserGen systems and methods, Nanopore-based platforms, chemical-sensitive field effect transistor (CHEMFET) array, electron microscopy-based sequencing (e.g., as developed by ZS Genetics, Halcyon Molecular), nanoball sequencing, the like or combinations thereof. Other sequencing methods that may be used to conduct methods herein include digital PCR, sequencing by hybridization, nanopore sequencing, chromosome-specific sequencing (e.g., using DANSR (digital analysis of selected regions) technology.

In various embodiments, the MPS process makes use of a solid phase comprising a flow cell on which nucleic acid from a library can be attached and reagents can be flowed and contacted with the attached nucleic acid. A flow cell includes flow cell lanes, and use of identifiers can facilitate analyzing a number of samples in each lane. A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs. In some embodiments the number of samples analyzed in a given flow cell lane is dependent on the number of unique identifiers utilized during library preparation and/or probe design. Multiplexing using 12 identifiers, for example, allows simultaneous analysis of 96 samples (e.g., equal to the number of wells in a 96 well microwell plate) in an 8 lane flow cell. Similarly, multiplexing using 48 identifiers, for example, allows simultaneous analysis of 384 samples (e.g., equal to the number of wells in a 384 well microwell plate) in an 8 lane flow cell. Non-limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively). In some embodiments, the samples are from different subjects and sequenced simultaneously as a batch run in a same flow cell. However, it should be understood that the samples from different subjects may be sequenced within multiple runs in different flow cells, combined and analyzed in a single batch or in multiple batches. However, this may introduce some variability into the process (e.g., artifacts due to batch-to-batch variations), which could cause a drop in performance.

At block 410, the sequence reads are mapped to genomic portions of a reference genome. Mapping sequence reads (i.e., sequence information from a fragment whose physical genomic position is unknown) can be performed in a number of ways, and often comprises alignment of the obtained sequence reads with a matching sequence in the reference genome. In such alignments, sequence reads generally are aligned to a reference sequence and those that align are designated as being "mapped," as "a mapped sequence read" or as "a mapped read." In certain embodiments, a mapped sequence read is referred to as a "hit" or "count." In some embodiments, mapped sequence reads are grouped together according to various parameters and assigned to particular genomic portions.

The terms "aligned," "alignment," or "aligning" generally refer to two or more nucleic acid sequences that can be identified as a match (e.g., 100% identity) or partial match. Alignments are performed by a computer (e.g., a software, program, module, or process), a non-limiting example of which includes the Efficient Local Alignment of Nucleotide Data (ELAND) computer program distributed as part of the Illumina Genomics Analysis pipeline. Alignment of a sequence read can be a 100% sequence match. In some cases, an alignment is less than a 100% sequence match (i.e., non-perfect match, partial match, partial alignment). In some embodiments an alignment is about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% match. In some embodiments, an alignment comprises a mismatch. In some embodiments, an alignment comprises 1, 2, 3, 4 or 5 mismatches. Two or more sequences can be aligned using either strand (e.g., sense or antisense strand). In certain embodiments a nucleic acid sequence is aligned with the reverse complement of another nucleic acid sequence.

Various computational methods can be used to align and map each sequence read to a genomic portion of the reference genome. Non-limiting examples of computer process that can be used to align sequences include, without limitation, BLAST, BLITZ, FASTA, BOWTIE 1, BOWTIE 2, ELAND, MAQ, PROBEMATCH, SOAP, BWA or SEQMAP, or variations thereof or combinations thereof. In some embodiments, sequence reads are aligned with sequences in a reference genome. In some embodiments, sequence reads are found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search identified sequences against a sequence database. Search hits can then be used to sort the identified sequences into appropriate portions (described hereafter), for example.

In some embodiments, a read may uniquely or non-uniquely map to portions in a reference genome. A read is considered as "uniquely mapped" if it aligns with a single sequence in the reference genome. A read is considered as "non-uniquely mapped" if it aligns with two or more sequences in the reference genome. In some embodiments, non-uniquely mapped reads are eliminated from further analysis (e.g. quantification). A certain, small degree of mismatch (0-1) may be allowed to account for single nucleotide polymorphisms that may exist between the reference genome and the reads from individual samples being mapped, in certain embodiments. In some embodiments, no degree of mismatch is allowed for a read mapped to a reference sequence.

As used herein, the term "reference genome" can refer to any particular known, sequenced or characterized genome, whether partial or complete, of any organism or virus which may be used to reference identified sequences from a subject. For example, a reference genome used for human subjects as well as many other organisms can be found at the National Center for Biotechnology Information at World Wide Web URL ncbi.nlm.nih.gov. A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. In some embodiments, a reference genome comprises sequences assigned to chromosomes.

At block 415, the mapped sequence reads may be grouped together according to various features and assigned to particular portions (e.g., portions of a reference genome). A "portion" also may be referred to herein as a "genomic section," "bin," "partition," "portion of a reference genome," "portion of a chromosome" or "genomic portion." A portion often is defined by partitioning of a genome according to one or more features. Non-limiting examples of certain partitioning features include length (e.g., fixed length, non-fixed length) and other structural features. Genomic portions sometimes include one or more of the following features: fixed length, non-fixed length, random length, non-random length, equal length, unequal length (e.g., at least two of the genomic portions are of unequal length), do not overlap (e.g., the 3' ends of the genomic portions sometimes abut the 5' ends of adjacent genomic portions), overlap (e.g., at least two of the genomic portions overlap), contiguous, consecutive, not contiguous, and not consecutive. Genomic portions sometimes are about 1 to about 1,000 kilobases in length (e.g., about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900 kilobases in length), about 5 to about 500 kilobases in length, about 10 to about 100 kilobases in length, or about 40 to about 60 kilobases in length.

Partitioning sometimes is based on, or is based in part on certain informational features, such as, information content and information gain, for example. Non-limiting examples of certain informational features include speed and/or convenience of alignment, sequencing coverage variability, GC content (e.g., stratified GC content, particular GC contents, high or low GC content), uniformity of GC content, other measures of sequence content (e.g., fraction of individual nucleotides, fraction of pyrimidines or purines, fraction of natural vs. non-natural nucleic acids, fraction of methylated nucleotides, and CpG content), methylation state, duplex melting temperature, amenability to sequencing or PCR, uncertainty value assigned to individual portions of a reference genome, and/or a targeted search for particular features. In some embodiments, information content may be quantified using a p-value profile measuring the significance of particular genomic locations for distinguishing between groups of confirmed normal and abnormal subjects (e.g. euploid and trisomy subjects, respectively).

In some embodiments, partitioning a genome may eliminate similar regions (e.g., identical or homologous regions or sequences) across a genome and only keep unique regions. Regions removed during partitioning may be within a single chromosome, may be one or more chromosomes, or may span multiple chromosomes. In some embodiments, a partitioned genome is reduced and optimized for faster alignment, often focusing on uniquely identifiable sequences.

In some embodiments, genomic portions result from a partitioning based on non-overlapping fixed size, which results in consecutive, non-overlapping portions of fixed length. Such portions often are shorter than a chromosome and often are shorter than a copy number variation region (e.g., a region that is duplicated or is deleted), the latter of which can be referred to as a segment. A "segment" or "genomic segment" often includes two or more fixed-length genomic portions, and often includes two or more consecutive fixed-length portions (e.g., about 2 to about 100 such portions (e.g., 2, 3, 4, 5, 6, 7, 8, 9, 10, 11, 12, 13, 14, 15, 16, 17, 18, 19, 20, 25, 30, 35, 40, 45, 50, 60, 70, 80, 90 such portions)).

Multiple portions sometimes are analyzed in groups, and sometimes reads mapped to portions are quantified according to a particular group of genomic portions. Where portions are partitioned by structural features and correspond to regions in a genome, portions sometimes are grouped into one or more segments and/or one or more regions. Non-limiting examples of regions include sub-chromosome (i.e., shorter than a chromosome), chromosome, autosome, sex chromosome and combinations thereof. One or more sub-chromosome regions sometimes are genes, gene fragments, regulatory sequences, introns, exons, segments (e.g., a segment spanning a copy number alteration region), microduplications, microdeletions and the like. A region sometimes is smaller than a chromosome of interest or is the same size of a chromosome of interest, and sometimes is smaller than a reference chromosome or is the same size as a reference chromosome.

At block 420, the sequence reads mapped to genomic portions are counted. The counting generates a quantification of the sequence reads mapped to the genomic portions of the reference genome. For example, sequence reads that are mapped or partitioned based on a selected feature or variable can be quantified to determine the amount or number of reads that are mapped to one or more portions (e.g., portion of a reference genome). In certain embodiments the quantity of sequence reads that are mapped to a portion or segment is referred to as a count or read density. A count often is associated with a genomic portion. In some embodiments a count is determined from some or all of the sequence reads mapped to (i.e., associated with) a portion. In certain embodiments, a count is determined from some or all of the sequence reads mapped to a group of portions (e.g., portions in a segment or region (described herein)).

A count can be determined by a suitable method, operation or algorithm. A count sometimes is the direct sum of all sequence reads mapped to a genomic portion or a group of genomic portions corresponding to a segment, a group of portions corresponding to a sub-region of a genome (e.g., copy number variation region, copy number duplication region, copy number deletion region, microduplication region, microdeletion region, chromosome region, autosome region, sex chromosome region) and/or sometimes is a group of portions corresponding to a genome. A read quantification sometimes is a ratio, and sometimes is a ratio of a quantification for portion(s) in region A to a quantification for portion(s) in region B. Region A sometimes is one portion, segment region, copy number variation region, copy number duplication region, copy number deletion region, microduplication region, microdeletion region, chromosome region, autosome region and/or sex chromosome region. Region B independently sometimes is one portion, segment region, copy number variation region, copy number duplication region, copy number deletion region, microduplication region, microdeletion region, chromosome region, autosome region, sex chromosome region, a region including all autosomes, a region including sex chromosomes and/or a region including all chromosome.

In some embodiments, a count is derived from raw sequence reads and/or filtered sequence reads. In certain embodiments a count is an average, mean or sum of sequence reads mapped to a genomic portion or group of genomic portions (e.g., genomic portions in a region). In some embodiments, a count is associated with an uncertainty value. A count sometimes is adjusted. A count may be adjusted according to sequence reads associated with a genomic portion or group of portions that have been weighted, removed, filtered, normalized, adjusted, averaged, derived as a mean, derived as a median, added, or combination thereof.

A sequence read quantification sometimes is a read density. A read density may be determined and/or generated for one or more segments of a genome. In certain instances, a read density may be determined and/or generated for one or more chromosomes. In some embodiments a read density comprises a quantitative measure of counts of sequence reads mapped to a segment or portion of a reference genome. A read density can be determined by a suitable process. In some embodiments a read density is determined by a suitable distribution and/or a suitable distribution function. Non-limiting examples of a distribution function include a probability function, probability distribution function, probability density function (PDF), a kernel density function (kernel density estimation), a cumulative distribution function, probability mass function, discrete probability distribution, an absolutely continuous univariate distribution, the like, any suitable distribution, or combinations thereof. A read density may be a density estimation derived from a suitable probability density function. A density estimation is the construction of an estimate, based on observed data, of an underlying probability density function. In some embodiments a read density comprises a density estimation (e.g., a probability density estimation, a kernel density estimation). A read density may be generated according to a process comprising generating a density estimation for each of the one or more portions of a genome where each portion comprises counts of sequence reads. A read density may be generated for normalized and/or weighted counts mapped to a portion or segment. In some instances, each read mapped to a portion or segment may contribute to a read density, a value (e.g., a count) equal to its weight obtained from a normalization process described herein. In some embodiments read densities for one or more portions or segments are adjusted. Read densities can be adjusted by a suitable method. For example, read densities for one or more portions can be weighted and/or normalized.

Reads quantified for a given portion or segment can be from one source or different sources. In one example, reads may be obtained from nucleic acid from a subject having cancer or suspected of having cancer. In such circumstances, reads mapped to one or more portions often are reads representative of both healthy cells (i.e., non-cancer cells) and cancer cells (e.g., tumor cells). In certain embodiments, some of the reads mapped to a portion are from cancer cell nucleic acid and some of the reads mapped to the same portion are from non-cancer cell nucleic acid. In another example, reads may be obtained from a nucleic acid sample from a pregnant female bearing a fetus. In such circumstances, reads mapped to one or more portions often are reads representative of both the fetus and the mother of the fetus (e.g., a pregnant female subject). In certain embodiments some of the reads mapped to a portion are from a fetal genome and some of the reads mapped to the same portion are from a maternal genome.

At block 425, one or more portions of the reference genome may be filtered or selected. The term "filtering" as used herein refers to removing portions or portions of a reference genome from consideration. In certain embodiments, one or more portions are filtered (e.g., subjected to a filtering process) thereby providing filtered portions. In some embodiments a filtering process removes certain portions and retains portions (e.g., a subset of portions).

Portions of a reference genome can be selected for removal based on any suitable criteria, including but not limited to redundant data (e.g., redundant or overlapping mapped reads), non-informative data (e.g., portions of a reference genome with zero median counts), portions of a reference genome with over represented or under represented sequences, noisy data, the like, or combinations of the foregoing. A filtering process often involves removing one or more portions of a reference genome from consideration and subtracting the counts in the one or more portions of a reference genome selected for removal from the counted or summed counts for the portions of a reference genome, chromosome or chromosomes, or genome under consideration. In some embodiments, portions of a reference genome can be removed successively (e.g., one at a time to allow evaluation of the effect of removal of each individual portion), and in certain embodiments all portions of a reference genome marked for removal can be removed at the same time. In some embodiments, portions of a reference genome characterized by a variance above or below a certain level are removed, which sometimes is referred to herein as filtering "noisy" portions of a reference genome. In certain embodiments, a filtering process comprises obtaining data points from a data set that deviate from the mean profile level of a portion, a chromosome, or part of a chromosome by a predetermined multiple of the profile variance, and in certain embodiments, a filtering process comprises removing data points from a data set that do not deviate from the mean profile level of a portion, a chromosome or part of a chromosome by a predetermined multiple of the profile variance. In some embodiments, a filtering process is utilized to reduce the number of candidate portions of a reference genome analyzed for the presence or absence of a genetic variation and/or copy number alteration (e.g., aneuploidy, microdeletion, microduplication). Reducing the number of candidate portions of a reference genome analyzed for the presence or absence of a genetic variation and/or copy number alteration often reduces the complexity and/or dimensionality of a data set, and sometimes increases the speed of searching for and/or identifying genetic variations and/or copy number alterations by two or more orders of magnitude.

Portions may be processed (e.g., filtered and/or selected) by any suitable method and according to any suitable parameter. Non-limiting examples of features and/or parameters that can be used to filter and/or select portions include redundant data (e.g., redundant or overlapping mapped reads), non-informative data (e.g., portions of a reference genome with zero mapped counts), portions of a reference genome with over represented or under represented sequences, noisy data, counts, count variability, coverage, mappability, variability, a repeatability measure, read density, variability of read density, a level of uncertainty, guanine-cytosine (GC) content, CCF fragment length and/or read length (e.g., a fragment length ratio (FLR), a fetal ratio statistic (FRS)), DNase1-sensitivity, methylation state, acetylation, histone distribution, chromatin structure, percent repeats, the like or combinations thereof. Portions can be filtered and/or selected according to any suitable feature or parameter that correlates with a feature or parameter listed or described herein. Portions can be filtered and/or selected according to features or parameters that are specific to a portion (e.g., as determined for a single portion according to multiple samples) and/or features or parameters that are specific to a sample (e.g., as determined for multiple portions within a sample). In some embodiments portions are filtered and/or removed according to relatively low mappability, relatively high variability, a high level of uncertainty, relatively long CCF fragment lengths (e.g., low FRS, low FLR), relatively large fraction of repetitive sequences, high GC content, low GC content, low counts, zero counts, high counts, the like, or combinations thereof. In some embodiments portions (e.g., a subset of portions) are selected according to suitable level of mappability, variability, level of uncertainty, fraction of repetitive sequences, count, GC content, the like, or combinations thereof. In some embodiments portions (e.g., a subset of portions) are selected according to relatively short CCF fragment lengths (e.g., high FRS, high FLR). Counts and/or reads mapped to portions are sometimes processed (e.g., normalized) prior to and/or after filtering or selecting portions (e.g., a subset of portions). In some embodiments counts and/or reads mapped to portions are not processed prior to and/or after filtering or selecting portions (e.g., a subset of portions).

In some embodiments, portions may be filtered according to a measure of error (e.g., standard deviation, standard error, calculated variance, p-value, mean absolute error (MAE), average absolute deviation and/or mean absolute deviation (MAD)). In certain instances, a measure of error may refer to count variability. In some embodiments portions are filtered according to count variability. In certain embodiments count variability is a measure of error determined for counts mapped to a portion (i.e., portion) of a reference genome for multiple samples (e.g., multiple sample obtained from multiple subjects, e.g., 50 or more, 100 or more, 500 or more 1000 or more, 5000 or more or 10,000 or more subjects). In some embodiments, portions with a count variability above a pre-determined upper range are filtered (e.g., excluded from consideration). In some embodiments portions with a count variability below a pre-determined lower range are filtered (e.g., excluded from consideration). In some embodiments, portions with a count variability outside a pre-determined range are filtered (e.g., excluded from consideration). In some embodiments portions with a count variability within a pre-determined range are selected (e.g., used for determining the presence or absence of a copy number alteration). In some embodiments, count variability of portions represents a distribution (e.g., a normal distribution). In some embodiments portions are selected within a quantile of the distribution. In some embodiments portions within a 99% quantile of the distribution of count variability are selected.

Sequence reads from any suitable number of samples can be utilized to identify a subset of portions that meet one or more criteria, parameters and/or features described herein. Sequence reads from a group of samples from multiple subjects sometimes are utilized. In some embodiments, the multiple subjects include pregnant females. In some embodiments, the multiple subjects include healthy subjects. In some embodiments, the multiple subjects include cancer patients. One or more samples from each of the multiple subjects can be addressed (e.g., 1 to about 20 samples from each subject (e.g., about 2, 3, 4, 5, 6, 7, 8, 9, 10, 11, 12, 13, 14, 15, 16, 17, 18 or 19 samples)), and a suitable number of subjects may be addressed (e.g., about 2 to about 10,000 subjects (e.g., about 10, 20, 30, 40, 50, 60, 70, 80, 90, 100, 150, 200, 250, 300, 350, 400, 500, 600, 700, 800, 900, 1000, 2000, 3000, 4000, 5000, 6000, 7000, 8000, 9000 subjects)). In some embodiments, sequence reads from the same test sample(s) from the same subject are mapped to portions in the reference genome and are used to generate the subset of portions.

Portions can be selected and/or filtered by any suitable method. In some embodiments portions are selected according to visual inspection of data, graphs, plots and/or charts. In certain embodiments portions are selected and/or filtered (e.g., in part) by a system or a machine comprising one or more microprocessors and memory. In some embodiments portions are selected and/or filtered (e.g., in part) by a non-transitory computer-readable storage medium with an executable program stored thereon, where the program instructs a microprocessor to perform the selecting and/or filtering.

In some embodiments, sequence reads derived from a sample are mapped to all or most portions of a reference genome and a pre-selected subset of portions are thereafter selected. For example, a subset of portions to which reads from fragments under a particular length threshold preferentially map may be selected. Certain methods for pre-selecting a subset of portions are described in U.S. Patent Application Publication No. 2014/0180594, which is incorporated by reference herein. Reads from a selected subset of portions often are utilized in further steps of a determination of the presence or absence of a genetic variation, for example. Often, reads from portions not selected are not utilized in further steps of a determination of the presence or absence of a genetic variation (e.g., reads in the non-selected portions are removed or filtered).

In some embodiments, portions associated with read densities (e.g., where a read density is for a portion) are removed by a filtering process and read densities associated with removed portions are not included in a determination of the presence or absence of a copy number alteration (e.g., a chromosome aneuploidy, microduplication, microdeletion). In some embodiments a read density profile comprises and/or consists of read densities of filtered portions. Portions are sometimes filtered according to a distribution of counts and/or a distribution of read densities. In some embodiments portions are filtered according to a distribution of counts and/or read densities where the counts and/or read densities are obtained from one or more reference samples. One or more reference samples may be referred to herein as a training set. In some embodiments portions are filtered according to a distribution of counts and/or read densities where the counts and/or read densities are obtained from one or more test samples. In some embodiments portions are filtered according to a measure of uncertainty for a read density distribution. In certain embodiments, portions that demonstrate a large deviation in read densities are removed by a filtering process. For example, a distribution of read densities (e.g., a distribution of average mean, or median read densities) can be determined, where each read density in the distribution maps to the same portion. A measure of uncertainty (e.g., a MAD) can be determined by comparing a distribution of read densities for multiple samples where each portion of a genome is associated with measure of uncertainty. According to the foregoing example, portions can be filtered according to a measure of uncertainty (e.g., a standard deviation (SD), a MAD) associated with each portion and a predetermined threshold. In certain instances, portions comprising MAD values within the acceptable range are retained and portions comprising MAD values outside of the acceptable range are removed from consideration by a filtering process. In some embodiments, according to the foregoing example, portions comprising read densities values (e.g., median, average or mean read densities) outside a pre-determined measure of uncertainty are often removed from consideration by a filtering process. In some embodiments portions comprising read densities values (e.g., median, average or mean read densities) outside an inter-quartile range of a distribution are removed from consideration by a filtering process. In some embodiments portions comprising read densities values outside more than 2 times, 3 times, 4 times or 5 times an inter-quartile range of a distribution are removed from consideration by a filtering process. In some embodiments portions comprising read densities values outside more than 2 sigma, 3 sigma, 4 sigma, 5 sigma, 6 sigma, 7 sigma or 8 sigma (e.g., where sigma is a range defined by a standard deviation) are removed from consideration by a filtering process.

At block 430, the mapped reads and counts thereof are output for downstream data processing such as normalization and CNV analysis, as described in detail with respect to FIGS. 5-7. Mapped sequence reads that have been counted are referred to herein as sequencing data. In some instances, the sequencing data represents unmanipulated counts (e.g., raw counts). In other instances, the sequencing data represents manipulated counts such as coverage for each reference base within a segment, a median coverage for each segment of the reference genome, and/or a sample median coverage ("global median coverage") for all segments in a sample. The base coverage for each reference base within a segment is determined based on the count of sequence reads mapped to each reference base within a segment. The median coverage for each segment is determined based on sorting the base coverage in a list from smallest to the largest (or largest to smallest) and finding a segment median coverage half-way down the sorted list. The sample median coverage for each sample is determined based on sorting the median coverage for each segment in a list from smallest to the largest (or largest to smallest) and finding the sample median coverage half-way down the sorted list, as described with respect to FIGS. 1 and 2. For calculating sample median coverage, segments on a sex chromosome could be excluded so that male and female samples could be analyzed together in the step of a second normalization. Alternatively, segment median coverage on Chromosome X for males could be doubled before being used for sample median coverage calculation, to ensure consistency between male samples and female samples in a second normalization. As described herein, it should be understood that other measures for a central tendency in a numerical data set or other statistical coverages such as mean coverage and mode coverage could also be used in place of median coverage for the segments and/or the global median coverage to obtain similar results with similar performance in many cases.

In some embodiments, sequence read data in a data set can be processed further (e.g., processed using mathematical approaches, statistical approaches, artificial intelligence approaches, or any combination thereof) and/or displayed to facilitate providing an outcome such as CNV analysis. In certain embodiments, data sets, including larger data sets, may benefit from pre-processing to facilitate further analysis. Pre-processing of data sets sometimes involves removal of redundant and/or uninformative portions or portions of a reference genome (e.g., portions of a reference genome with uninformative data, redundant mapped reads, portions with zero median counts, over represented or under represented sequences), or removal/exclusion of uninformative or noisy segments. Without being limited by theory, data processing and/or preprocessing may (i) remove noisy data, (ii) remove uninformative data, (iii) remove redundant data, (iv) reduce the complexity of larger data sets, and/or (v) facilitate transformation of the data from one form into one or more other forms. The terms "pre-processing" and "processing" when utilized with respect to data or data sets are collectively referred to herein as "processing." Processing can render data more amenable to further analysis, and can generate an outcome in some embodiments. In some embodiments one or more or all processing methods (e.g., normalization methods, portion filtering, mapping, validation, the like or combinations thereof) are performed by a processor, a micro-processor, a computer, in conjunction with memory and/or by a microprocessor controlled apparatus.

The term "noisy data" as used herein refers to (a) data that has a significant variance between data points when analyzed or plotted, (b) data that has a significant standard deviation (e.g., greater than 3 standard deviations), (c) data that has a significant standard error of the mean, the like, and combinations of the foregoing. Noisy data sometimes occurs due to the quantity and/or quality of starting material (e.g., nucleic acid sample), and sometimes occurs as part of processes for preparing or replicating DNA used to generate sequence reads. In certain embodiments, noise results from certain sequences being overrepresented when prepared using PCR-based methods. Methods described herein can reduce or eliminate the contribution of noisy data, and therefore reduce the effect of noisy data on the provided outcome.

The terms "uninformative data," "uninformative portions of a reference genome," and "uninformative portions" as used herein refer to portions, or data derived therefrom, having a numerical value that is significantly different from a predetermined threshold value or falls outside a predetermined cutoff range of values. The terms "threshold" and "threshold value" herein refer to any number that is calculated using a qualifying data set and serves as a limit of diagnosis of a genetic variation (e.g., a copy number alteration, an aneuploidy, a microduplication, a microdeletion, a chromosomal aberration, and the like). In certain embodiments, a threshold is exceeded by results obtained by methods described herein and a subject is diagnosed with a copy number alteration. A threshold value or range of values often is calculated by mathematically and/or statistically manipulating sequence read data (e.g., from a reference and/or subject), in some embodiments, and in certain embodiments, sequence read data manipulated to generate a threshold value or range of values is sequence read data (e.g., from a reference and/or subject). In some embodiments, an uncertainty value is determined. An uncertainty value generally is a measure of variance or error and can be any suitable measure of variance or error. In some embodiments an uncertainty value is a standard deviation, standard error, calculated variance, p-value, or mean absolute deviation (MAD). In some embodiments an uncertainty value can be calculated according to a formula described herein.

Any suitable procedure can be utilized for processing data sets described herein. Non-limiting examples of procedures suitable for use for processing data sets include filtering, normalizing, weighting, monitoring peak heights, monitoring peak areas, monitoring peak edges, peak level analysis, peak width analysis, peak edge location analysis, peak lateral tolerances, determining area ratios, mathematical processing of data, statistical processing of data, application of statistical process, analysis with fixed variables, analysis with optimized variables, plotting data to identify patterns or trends for additional processing, the like and combinations of the foregoing. In some embodiments, data sets are processed based on various features (e.g., GC content, redundant mapped reads, centromere regions, telomere regions, the like and combinations thereof) and/or variables (e.g., subject gender, subject age, subject ploidy, percent contribution of cancer cell nucleic acid, fetal gender, maternal age, maternal ploidy, percent contribution of fetal nucleic acid, the like or combinations thereof). In certain embodiments, processing data sets as described herein can reduce the complexity and/or dimensionality of large and/or complex data sets. A non-limiting example of a complex data set includes sequence read data generated from one or more test subjects and a plurality of reference subjects of different ages and ethnic backgrounds. In some embodiments, data sets can include from thousands to millions of sequence reads for each test and/or reference subject.

Data processing can be performed in any number of steps, in certain embodiments. For example, data may be processed using only a single processing procedure in some embodiments, and in certain embodiments data may be processed using 1 or more, 5 or more, 10 or more or 20 or more processing steps. In some embodiments, one or more processing steps can comprise one or more normalization steps Normalization can be performed by a suitable method described herein or known in the art, as conventionally performed in the analysis of gene expression data and microarray data. In certain embodiments, normalization comprises adjusting values measured on different scales to a notionally common scale. In certain embodiments, normalization comprises a sophisticated mathematical adjustment to bring probability distributions of adjusted values into alignment. In some embodiments normalization comprises aligning distributions to a normal distribution. In certain embodiments normalization comprises mathematical adjustments that allow comparison of corresponding normalized values for different datasets in a way that eliminates the effects of certain gross influences (e.g., error and anomalies). In certain embodiments normalization comprises scaling. Normalization sometimes comprises division of one or more data sets by a predetermined variable or formula. Normalization sometimes comprises subtraction of one or more data sets by a predetermined variable or formula. Non-limiting examples of normalization methods include portion-wise normalization, normalization by GC content, median count (median bin count, median portion count) normalization, linear and nonlinear least squares regression, LOESS, LOESSM, GC LOESS, LOWESS (locally weighted scatterplot smoothing), principal component normalization, repeat masking (RM), GC-normalization and repeat masking (GCRM), cQn and/or combinations thereof. In some embodiments, the determination of a presence or absence of a copy number alteration (e.g., an aneuploidy, a microduplication, a microdeletion) utilizes a normalization method (e.g., portion-wise normalization, normalization by GC content, median count (median bin count, median portion count) normalization, linear and nonlinear least squares regression, LOESS, LOESSM, GC LOESS, LOWESS (locally weighted scatterplot smoothing), principal component normalization, repeat masking (RM), GC-normalization and repeat masking (GCRM), cQn, a normalization method known in the art and/or a combination thereof). Described in greater detail hereafter is a specific two-step normalization processes that can be utilized.

IIID. A First Normalization—"Within a Sample Normalization"

After obtaining sequencing data, including a median coverage for each segment in each of the samples, a first normalization is performed. The first normalization is performed to provide a normalized number for each segment or element in a sample representing a relative level of coverage for the segment or element in the sample. In various embodiments, all segments in each sample will be considered in the first normalization step. In some embodiments, a target set may be predetermined and only segments/elements in the target set may be considered in the first normalization. An element in the target set is (i) a gene, (ii) a chromosome, (iii) a portion of a chromosome, (iv) an exon, (v) an intron, or (v) a predetermined genomic part or region of interest. In some instances, all elements in the target set are of the same type. In other instances, the elements in the target set are of different types.

FIG. 5 is a flowchart illustrating a process 500 for performing a first normalization and obtaining normalized segment (or element) median coverage ratios according to various embodiments. The processing depicted in FIG. 5 may be implemented in software (e.g., code, instructions, program) executed by one or more processing units (e.g., processors, cores) of the respective systems, hardware, or combinations thereof. The software may be stored on a non-transitory storage medium (e.g., on a memory device). The method presented in FIG. 5 and described below is intended to be illustrative and non-limiting. Although FIG. 5 depicts the various processing steps occurring in a particular sequence or order, this is not intended to be limiting. In certain alternative embodiments, the steps may be performed in some different order or some steps may also be performed in parallel. In certain embodiments, such as in the embodiment depicted in FIG. 3, the processing depicted in FIG. 5 may be performed by a computing device such as a computer.

In process 500, each sample is processed independently. At block 505, information comprising: (i) a median coverage for each segment of each sample, and (ii) a global median for each sample, and/or a predetermined target set is obtained. In various embodiments, some or all the obtained information is the sequencing data provided by following a method disclosed in process 400 in FIG. 4 or the like. In some embodiments, some or all obtained information is provided by a separate block of process 100 in FIG. 1. In some embodiments, some or all obtained information is provided by an external module or through a user-interaction device. The predetermined target set provides information of region of interest (ROI) to be analyzed in CNV detection. Each element in the predetermined target set may be (i) a gene, (ii) a chromosome, (iii) a partial chromosome, (iv) an exon, (v) an intron, or (v) a predetermined genomic region of interest. In various embodiments, an element in a target set is not a segment. In some embodiments, at least one element in a target set is a segment. If one or more elements in the predetermined target set are not segments, a block 510 is required to determine a local median coverage for each of the one or more element.

At block 510, coverages of segments covered by each element in the predetermined target set are obtained and sorted to determine a local median coverage for each of the elements in the predetermined target set. Because one or more elements in the predetermined target set are not segments, each of the one or more elements covers at least two segments. For segments covered in each of the one or more elements, their corresponding coverages are sorted in a list and counted half-way down the list to find a median among the coverages for each element. The median is a local median coverage for the element. For example, if a coverage for each segment covered in an element is 7, 4, and 9 respectively, then the sorted coverages are 4, 7, and 9, thus 7 is the median and the local median coverage for the element. In some instances, when an element is a segment, the coverage for the segment is the local median coverage for the element. In various embodiments, a local median coverage is determined for each element in a predetermined target set. In some embodiments, a local median coverage is determined for each element that is not a segment in a predetermined target set.

At block 515, each coverage or local median coverage is normalized by the global median coverage obtained at block 505 ("scaling towards the global median"). In various embodiments, the obtained coverage for each segment or the determined local median coverage for each element in the predetermined target set is divided by the global median coverage to obtain a normalized segment median coverage ratio for the segment or a normalized element median coverage ratio for the element in the predetermined target set. In some embodiments, the normalized segment median coverage ratio or the normalized element median coverage ratio may be rounded to a predetermined accuracy. It should be appreciated that the normalized segment median coverage ratio or the normalized element median coverage ratio may be determined by a similar mathematical manner as the division.

At block 520, the normalized segment (or element) median coverage ratios are provided for processing a second normalization. The provided information may further include the predetermined target set information. As provided herein, the normalized segment (or element) median coverage ratios may be based on median values of coverages. In most instances, a median coverage is better than a mean coverage because the raw coverage counts are not normally distributed. However, it should be appreciated that in some instances, a mean coverage can substitute the median coverage in performing a first normalization or in obtaining a global median coverage. It should also be appreciated that in some instances, a statistical measure functioning similar to a median can substitute the median coverage in performing a first normalization or in obtaining a global median coverage.

III.E. A Second Normalization—"Across Samples Normalization"

After determining a normalized segment (or element) median coverage ratios in the samples, a second normalization follows. The second normalization is performed to provide a copy number for each segment (or element) across samples representing a relative level of coverage for each segment (or element) in the sample, where the copy number has a more standardized number that is rarely impacted by a type or location of the corresponding element. In various embodiments, each of the segments in all samples or each of the elements in all samples will be considered in the second normalization. In some embodiment, a target set may be predetermined and only segments/elements in the target set may be considered in the second normalization. An element in the target set is (i) a gene, (ii) a chromosome, (iii) a portion of a chromosome, (iv) an exon, (v) an intron, or (v) a predetermined genomic part or region of interest. In some instances, all elements in the target set are of the same type. In other instances, the elements in the target set are of different types. In many instances, the target set in the second normalized is the same target set as that in the first normalization. It should be appreciated that the target set in the second normalization can be different than the target set in the first normalization.

FIG. 6 is a flowchart illustrating a process 600 for performing a second normalization and obtaining copy number coverages according to various embodiments. The processing depicted in FIG. 6 may be implemented in software (e.g., code, instructions, program) executed by one or more processing units (e.g., processors, cores) of the respective systems, hardware, or combinations thereof. The software may be stored on a non-transitory storage medium (e.g., on a memory device). The method presented in FIG. 6 and described below is intended to be illustrative and non-limiting. Although FIG. 6 depicts the various processing steps occurring in a particular sequence or order, this is not intended to be limiting. In certain alternative embodiments, the steps may be performed in some different order or some steps may also be performed in parallel. In certain embodiments, such as in the embodiment depicted in FIG. 3, the processing depicted in FIG. 6 may be performed by a computing device such as a computer.

In process 600, all samples within a batch (e.g., a flowcell batch) are processed jointly to perform a second normalization. In some embodiments, the samples are from different subjects and sequenced simultaneously as a batch run, for example, in a same flow cell. In other embodiments, the samples are from different subjects sequenced within multiple batch runs, for example, in different flow cells. The minimum number of samples from a same or different batches to be used jointly for the second normalization is at least five samples, preferably at least ten samples. At block 605, information comprising normalized segment (or element) median coverage ratios for a same segment (or element) in all samples in a batch and/or a predetermined target set is obtained. In various embodiments, some or all the obtained information is the sequencing data provided by following a method disclosed in process 500 in FIG. 5 or the like. In some embodiments, some or all obtained information is provided by a separate block of process 100 in FIG. 1. In some embodiments, some or all obtained information is provided by an external module or through a user-interaction device. The predetermined target set provides information of region of interest (ROI) to be analyzed in CNV detection. Each element in the predetermined target set may be (i) a gene, (ii) a chromosome, (iii) a partial chromosome, (iv) an exon, (v) an intron, or (vi) a predetermined genomic region of interest. In various embodiments, an element in a target set is not a segment. In some embodiments, at least one element in a target set is a segment. In various embodiments, the target set in the second normalized is the same target set as that in the first normalization process 500. In some instances, the target sets may be different.

At block 610, a mean coverage for the same segment (or element) is determined for all the samples in the same batch. In some embodiments, the mean coverage for the segment (or element) is determined by calculating the sum of the normalized segment (or element) median coverage ratio of the segment (or element) in each sample and dividing the sum by the number of the samples. In various embodiments, all the normalized segment (or element) median coverage ratios of the segment (or element) are considered to form a mathematical set and outliers to the mathematical set are excluded before calculating the mean coverage for the segment (or element). The outliers are determined by a predetermined rule. In various embodiments, the predetermined rule comprises (i) determining a Q1 by picking up a 25 percentile value from the mathematical set, (ii) determining a Q3 by picking up a 25 percentile value from the mathematical set, (iii) calculating an interquartile range ("IQR") for the set by subtracting Q1 from Q3; and (iv) determining if there is any value greater than Q3 plus 1.5 times of IQR or less than Q1 minus 1.5 times of IQR. An outlier is determined and excluded from the calculation of the mean coverage if its first normalized coverage is greater than Q3 plus 1.5 times of IQR or less than Q1 minus 1.5 times of IQR. In some instances, 1.5 can be substitute by any positive number (e.g., 2 or 1.2). In some instances, a similar rule as Tukey's Fences may be used to decide outliers. In some instances, a normal distribution or the like may be constructed based on the mathematical set to decide outliers. In most instances, a mean coverage is compatible to perform the second normalization because after the first normalization and/or exclusion of outliers, remaining first normalized coverage is roughly distributed symmetrically. It should also be appreciated that in some instances, a statistical measure functioning similar to a mean can substitute the mean coverage in performing the second normalization.

At block 615, each normalized segment (or element) median coverage ratio is normalized by the mean coverage determined at block 610. In various embodiments, the normalized segment (or element) median coverage ratio is divided by the mean coverage to get a copy number for the segment (or element). In some embodiments, the copy number may be rounded to a predetermined accuracy. It should be appreciated that the copy number may be determined by a similar mathematical manner as the division.

At block 620, the copy numbers for all segments/elements are provided for processing a CNV detection. In parallel with the copy numbers, a normal profile for a segment (or element) comprising all copy numbers for the same segment (or element) in all samples in a same batch or across different batches are provided and prepared to be used in the CNV detection. The provided information may further include the predetermined target set information.

III.F. Copy Number Variation Detection

After determining a copy number for each segment or each element in each of the samples, a CNV detection follows. In some instances, the detection is performed regarding each element in a target sample. In some instances, the detection is performed regarding each segment in a target sample. In some instances, the detection is performed regarding one or more elements in a predetermined target set in a target sample. In some instances, the detection is performed regarding one or more segments in a predetermined target set in a target sample. A predetermined target set (e.g., a first target set, or a second target set) may comprise (i) a gene, (ii) a chromosome, (iii) a portion of a chromosome, (iv) an exon, (v) an intron, or (vi) a predetermined genomic part or region of interest. The predetermined target set may be a same set as the target set in the first normalization or the second normalization. Hereinafter of this part (Part III.F), for simplification and clarification, the term "element" refers to a segment, a gene, a chromosome, a portion of a chromosome, an exon, an intron, a predetermined genomic portion or ROI and "each element in a target sample" comprises "elements in a predetermined target set in a target sample."

The absence or presence of CNV is detected using artificial intelligence techniques. The artificial intelligence techniques including rule-based methods, machine learning models, or a combination thereof. The CNV detection is based on the results of the second normalization, specifically copy number per segment (or element), or the p-value (or the corresponding z-score, or a statistical measure) for the segment (or element) or both the copy number and the p-value (or the corresponding z-score, or a statistical measure), plus the raw coverage and the GC-contents. In various embodiments, a CNV detection for a target sample uses only a copy number for each element in the target sample. In some embodiments, the CNV detection step for a target sample uses both the second normalized coverage for each element in the target sample and a statistical measure for each element in the target sample. In some instances, the statistical measure is a z-score or a p-value calculated based on a normal profile, where the normal profile comprises the copy number for each element in each of the samples in a same batch or across different batches. In other instances, the statistical measure is a coefficient of variation calculated based on the normal profile. It should be appreciated that any statistical measure functioning similar to a p-value, a z-score, or a coefficient of variation can be used in the CNV detection.

FIG. 7 is a block diagram illustrating a machine learning system 700 in accordance with various embodiments. As shown in FIG. 7, the machine learning system 700 includes various stages: a prediction model training stage 710 to build and train models, an evaluation stage 715 to evaluate performance of trained models, and an implementation stage 720 for implementing one or more models using a computing system (e.g., computing system 300). The prediction model training stage 710 builds and trains one or more prediction models **725*a*-725*n* ('n' represents any natural number) to be used by the other stages (which may be referred to herein individually as a prediction model 725 or collectively as the prediction models 725). For example, the prediction models 725** can include a model for predicting the absence or presence of CNV within a sample. Still other types of prediction models may be implemented in other examples according to this disclosure.

A prediction model 725 can be a machine learning ("ML") model, such as a convolutional neural network ("CNN"), e.g., an inception neural network, a residual neural network ("Resnet"), or a recurrent neural network, e.g., long short-term memory ("LSTM") models or gated recurrent units ("GRUs") models, other variants of Deep Neural Networks ("DNN") (e.g., a multi-label n-binary DNN classifier or multi-class DNN classifier). A prediction model 725 can also be any other suitable ML model trained for providing a prediction, such as a Generalized linear model (GLM), Support Vector Machine, Bagging Models such as Random Forest Model, Boosting Models, Shallow Neural Networks, or combinations of one or more of such techniques—e.g., CNN-HMM or MCNN (Multi-Scale Convolutional Neural Network). The machine learning system 700 may employ the same type of prediction model or different types of prediction models for providing predictions to users. In certain instances, the prediction model 725 performs CNV analysis using a random forest model. Still other types of prediction models may be implemented in other examples according to this disclosure.

To train the various prediction models 725, the training stage 710 is comprised of two main components: dataset preparation module 730 and model training framework 740. The dataset preparation module 730 performs the processes of loading data assets 745, splitting the data assets 745 into training and validation sets **745*a-n* so that the system can train and test the prediction models 725, and pre-processing of data assets 745. The splitting the data assets 745 into training and validation sets 745*a-n*** may be performed randomly (e.g., a 90/10% or 70/30%) or the splitting may be performed in accordance with a more complex validation technique such as K-Fold Cross-Validation, Leave-one-out Cross-Validation, Leave-one-group-out Cross-Validation, Nested Cross-Validation, or the like to minimize sampling bias and overfitting.

The training data **745*a* may include at least a subset of data from prior samples. The data includes raw coverage values, median coverage values as described with respect to the first normalization, mean coverage values as described with respect to the second normalization, copy numbers and a normal profile for each element in a sample, p-value, a z-score, and/or a coefficient of variation for each element in a sample, the GC-content for each element in a sample, or any combination thereof. The data can be obtained in various ways including image or text. For example, if the historical data is provided as images of sequencing data, the data preparation 730 may convert the images to text using an image-to-text converter (not shown) that performs text recognition (e.g., optical character recognition) to determine the text within the image. Additionally or alternatively, the data preparation module 730 may standardize the format of the data. In some instances, the data is provided by a second party or a third party for purposes of training a prediction model. The training data 745*a* for a prediction model 825 may include the historical data and labels 850 corresponding to the true positives of true negatives for absence or presence of CNV. For example, for each sample, an indication of the correct CNV call to be inferred by the prediction model 725 may be provided as ground truth information for labels 750. In some instances, the labels 750 may be obtained from a data structure used to maintain data consistency across training samples. The behavior of the prediction model 725** can then be adapted (e.g., through back-propagation) to minimize the difference between the generated inferences for various entities and the ground truth information.

The model training framework 740 performs the processes of determining hyperparameters for the model 725 and performing iterative operations of inputting examples from the training data **745*a* into the model 725 to find a set of model parameters (e.g., weights and/or biases) that minimizes a cost function(s) such as loss or error function for the model 725. The hyperparameters are settings that can be tuned or optimized to control the behavior of the model 725. Most models explicitly define hyperparameters that control different features of the models such as memory or cost of execution. However, additional hyperparameters may be defined to adapt the model 725 to a specific scenario. For example, the hyperparameters may include the number of hidden units of a model, the learning rate of a model, the convolution kernel width, the number of kernels for a model, the maximum depth of a tree in a random forest, a minimum sample split, a maximum number of leaf nodes, a minimum number of leaf nodes, and the like. The cost function can be constructed to measure the difference between the outputs inferred using the models 745** and the ground truth annotated to the samples using the labels. For example, for a supervised learning-based model, the goal of the training is to learn a function "h( )" (also sometimes referred to as the hypothesis function) that maps the training input space X to the target value space Y, h: X→Y, such that h(x) is a good predictor for the corresponding value of y. Various different techniques may be used to learn this hypothesis function. In some techniques, as part of deriving the hypothesis function, the cost or loss function may be defined that measures the difference between the ground truth value for an input and the predicted value for that input. As part of training, techniques such as back propagation, random feedback, Direct Feedback Alignment (DFA), Indirect Feedback Alignment (IFA), Hebbian learning, and the like are used to minimize this cost or loss function.

Once the set of model parameters are identified, the model 725 has been trained and the model training framework 740 performs the additional processes of testing or validation using the subset of testing data 745*b* (testing or validation data set). The testing or validation processes includes iterative operations of inputting utterances from the subset of testing data 745*b* into the model 725 using a validation technique such as K-Fold Cross-Validation, Leave-one-out Cross-Validation, Leave-one-group-out Cross-Validation, Nested Cross-Validation, or the like to tune the hyperparameters and ultimately find the optimal set of hyperparameters. Once the optimal set of hyperparameters are obtained, a reserved test set from the subset of test data 745*a* may be input into the model 725 to obtain output (in this example, one or more recognized entities), and the output is evaluated versus ground truth entities using correlation techniques such as Bland-Altman method and the Spearman's rank correlation coefficients. Further, performance metrics 755 may be calculated in evaluation stage 715 such as the error, accuracy, precision, recall, receiver operating characteristic curve (ROC), etc. The metrics 755 may be used in the evaluation stage 715 to analyze performance of the model 725 for providing recommendations.

The model training stage 710 outputs trained models including one or more trained prediction models 760. The one or more trained prediction models 755 may be deployed and used in the implementation stage 720 for providing predictions 765 to users (as described in detail with respect to FIG. 8). For example, prediction models 760 may receive input data 770 including raw coverage values, median coverage values as described with respect to the first normalization, mean coverage values as described with respect to the second normalization, copy numbers and a normal profile for each element in a sample, p-value, a z-score, and/or a coefficient of variation for each element in a sample, the GC % for each element in a sample, or any combination thereof and provide predictions 765 to a user based on an estimated CNVs.

FIG. 8 is a flowchart illustrating a process 800 for performing and reporting a CNV detection according to various embodiments. The processing depicted in FIG. 8 may be implemented in software (e.g., code, instructions, program) executed by one or more processing units (e.g., processors, cores) of the respective systems, hardware, or combinations thereof. The software may be stored on a non-transitory storage medium (e.g., on a memory device). The method presented in FIG. 8 and described below is intended to be illustrative and non-limiting. Although FIG. 8 depicts the various processing steps occurring in a particular sequence or order, this is not intended to be limiting. In certain alternative embodiments, the steps may be performed in some different order or some steps may also be performed in parallel. In certain embodiments, such as in the embodiments depicted in FIGS. 3 and 7, the processing depicted in FIG. 8 may be performed by a computing device such as a computer using artificial intelligence based approaches.

At block 805, information comprising a copy number for each element in a target sample and a normal profile for each is obtained. In various embodiments, a normal profile for an element comprises all copy numbers for the element in all samples in a same batch or across different batches where the target sample is synthesized. In some embodiments, a normal profile for an element comprises all copy numbers, excluding outliers for the element in all samples in same batch or across different batches where the target sample is synthesized. In various embodiments, some or all obtained information at block 605 is provided by following a method disclosed in process 600 in FIG. 6 or the like. In some embodiments, some or all obtained information is provided by a separate block of process 100 in FIG. 1. In some embodiments, some or all obtained information is provided by an external module or through a user-interaction device.

Block 810 is an optional block if a more accurate result is pursued. At block 810, A p-value for an element in the target sample is determined based on a normal profile for the element. The normal profile for the element obtained at block 705 comprises the copy numbers for the element in each of the samples in the same batch where the target sample is synthesized. The p-value for the element in the target sample may be determined in a normal way that a p-value is determined. In various embodiments, the detection of CNVs for a target sample may be also based on a statistical measure of a copy number for each element in the target sample. In some instances, the statistical measure is p-value. In some instances, the statistical measure is z-score. It should be appreciated that the statistical measure is not limited to p-value or z-score. Any statistical measure having a similar function as p-value may be used in the CNV detection step. Hereinbefore and hereinafter of this part (Part III.F), the term "p-value" refers to any statistical measure as defined in this paragraph.

In accordance with rule-based approaches, at block 815, information comprising a predetermined interval for an abnormal copy number detection and/or a predetermine upper-threshold/lower-threshold for an abnormal p-value detection is obtained. The obtained information provides a threshold for comparison in the following steps.

In accordance with rule-based approaches, at block 820, a copy number for an element is compared with the predetermined interval obtained at block 715. A detection of CNVs for a target sample is based on a copy number for each element in the target sample. A copy number for an element in the target sample is compared to a predetermined interval to see if the copy number falls into the predetermined interval. The copy number for an element is treated as an abnormal copy number if the copy number does not fall into the predetermined interval. For example, a predetermined interval may be [0.7, 1.3]. If the copy number is greater than 1.3 or small than 0.7, it is treated as abnormal, and the corresponding element in the target sample may be marked and temporarily stored in a memory.

Also in accordance with rule-based approaches, at block 820, a copy number for an element may also be compared with the predetermined upper-threshold/lower-threshold obtained at block 815. If the p-value for the element in the target sample is less than the predetermined lower-threshold, the p-value is considered significant (an abnormal copy number). For example, an obtained predetermined lower-threshold may be 0.0003. If a p-value for an element is 0.0001, the element in the target sample is determined to have an abnormal copy number and its p-value may be marked and temporarily stored in a memory.

Also in accordance with rule-based approaches, at block 825, a determination of CNV detection is made and reported based on the comparison result obtained at 820. In various embodiments, a detection of a presence of CNV is reported if both criteria are met: an abnormal copy number for an element in a target sample is found or marked, and an abnormal p-value for the element in the target sample is also found or marked. A detection report for the element in the target sample is generated, where the report may comprise an ID for the target sample, an indicium (e.g., name or location) of the element, a copy number for the element, and/or a p-value for the element. In some instances, other information relating to the target sample may also be reported, e.g., gender of the target sample, gene indicium of the element if the element is an exon, a type of the CNV detection (e.g., cnvdup or cnvdel), or the like. In some embodiments, a detection of an absence of CNV is reported if not both criteria are met: an abnormal copy number for an element in a target sample is found or marked, and an abnormal p-value for the element in the target sample is also found or marked. A detection report for the element in the target sample is generated, where the report may comprise an ID for the target sample, an indicium (e.g., name or location) of the element, a copy number for the element, a p-value for the element, and/or an absence status of CNV detection in the element. In some instances, other information relating to the target sample may also be reported, e.g., gender of the target sample, gene indicium of the element if the element is an exon, or the like. In some embodiments, if at least one of the criteria is not met and the copy number or the p-value is close enough to the corresponding threshold value (e.g., boundary values of a predetermined interval, a predetermined upper-threshold, or a predetermined lower-threshold), the detection report may also comprise this information. In some embodiments, a combined detection report for all elements in the target sample may be generated instead of each detection report for one element in the target sample. In some embodiments, a combined detection report for all elements in multiple target samples may be generated instead of each detection report for one element in each of the multiple target samples.

In some embodiments, a detection of CNV is reported if at least one of the criteria is met: an abnormal copy number for an element in a target sample is found or marked, or an abnormal p-value for the element in the target sample is found or marked. A detection report for the element in the target sample is generated, where the report may comprise an ID for the target sample, an indicium (e.g., name or location) of the element, a copy number for the element, and/or a p-value for the element. In some instances, other information relating to the target sample may also be reported, e.g., gender of the target sample, gene indicium of the element if the element is an exon, a type of the CNV detection (e.g., cnvdup or cnvdel), or the like. In some embodiments, a detection of an absence of CNV is reported if neither criteria are met: an abnormal copy number for an element in a target sample is found or marked, and an abnormal p-value for the element in the target sample is found or marked. A detection report for the element in the target sample is generated, where the report may comprise an ID for the target sample, an indicium (e.g., name or location) of the element, a copy number for the element, a p-value for the element, and/or an absence status of CNV detection in the element. In some instances, other information relating to the target sample may also be reported, e.g., gender of the target sample, gene indicium of the element if the element is an exon, or the like. In some embodiments, if neither criteria are met and the copy number or the p-value is close enough to the corresponding threshold value (e.g., boundary values of a predetermined interval, a predetermined upper-threshold, or a predetermined lower-threshold), the detection report may also comprise this information. In some embodiments, a combined detection report for all elements in the target sample may be generated instead of each detection report for one element in the target sample. In some embodiments, a combined detection report for all elements in multiple target samples may be generated instead of each detection report for one element in each of the multiple target samples.

In accordance with machine learning-based approaches, at block 830, raw coverage values, median coverage values as described with respect to the first normalization, mean coverage values as described with respect to the second normalization, copy numbers and a normal profile for each element in a sample, p-value, a z-score, and/or a coefficient of variation for each element in a sample, the GC % for each element in a sample, or any combination thereof are input into the machine learning model. In some instances, at least the copy numbers and a normal profile for each element in a sample are input into the machine learning model. In certain instances, the machine learning model is a random forest model comprised of a number of individual decision trees that operate as an ensemble to split observations based on learned features in order to classify the copy number for each element as indicative of a presence or absence of the copy number variation. Additionally, the machine learning model may be configured to classify the presence of the copy number variation (i.e., an abnormal copy number) for an element as either a duplication or a deletion. The machine-learning model outputs a classification for the presence or absence of the copy number variation for each segment (optionally classification of abnormal as duplication or deletion) in a target set according to the operation of the decision trees. Advantageously, the machine-learning based approach trained on previously confirmed copy number variation samples has better sensitivity and specificity compared to the rule-based approaches, and does not require hard cutoffs or thresholds for p-values and double normalized copy numbers to call the copy number variations.

At block 835, a detection of CNV is reported based on the classification for an element by the machine learning model. In some instances, the detection of CNV is reported based on the comparing (described with respect to steps 820 and 825), the classifying by the machine learning model, or a combination thereof. For example, if both the rule-based approaches and the machine learning based approaches are in agreement concerning the classification of the element, then the detection of CNV is reported. Alternatively, if the rule-based approaches and the machine learning based approaches are in disagreement concerning the classification of the element, then the detection of CNV is reported as inconclusive. Alternatively, if the rule-based approaches and the machine learning based approaches are in disagreement concerning the classification of the element, then the detection of CNV is referred for manual interpretation or a reflex testing. A detection report for the element in the target sample is generated, where the report may comprise an ID for the target sample, an indicium (e.g., name or location) of the element, a copy number for the element, and/or a p-value for the element. In some instances, other information relating to the target sample may also be reported, e.g., gender of the target sample, gene indicium of the element if the element is an exon, a type of the CNV detection (e.g., cnvdup or cnvdel), or the like.

The detection report or the combined detection report from the rule-based approaches, machine learning-based approaches, or a combination thereof can be further used as a pre-analysis of the target sample or can provide information for post-analysis of the target sample. In some embodiments, the detection report may be used in determining a diagnosis of a subject associated with the target sample. The diagnosis may be based on the presence or absence of CNV calling on the target sample. In some embodiment, the detection report may be used in administering a treatment to a subject associated with the target sample. The administration may be based on the presence or absence of CNV calling on the target sample, or based on the diagnosis of the subject associated with the target sample. It should be appreciated that the post-analysis of the target sample is not limited to a diagnosis or an administration and the CNV detection method may be combined or configured to any post-analysis method.

IV. EXAMPLES

The techniques implemented in various embodiments may be better understood by referring to the following examples.

IV.A. A Pseudo-Example of Performing Double-Normalization

After obtaining sequencing data for a plurality of samples, including a target sample, it is ready to perform the disclosed double-normalization. FIGS. 9A-9D provide a pseudo example of the double-normalization.

FIG. 9A illustrates a means to determine a local median coverage for each element in a target set in a sample and to determine a global median coverage for all segments in the sample. Sample 1 is one of the plurality of the samples and its sequencing data, including a median coverage for each segment, has been obtained through MPS sequencing methods. A target set has been determined for detection of a certain type of CNVs. In some instances, elements in the target set are chromosomes and each chromosome covers a number of different segments, and there is no overlapped segment between two different elements. In some instances, elements in the target set are genes and different genes may cover a same segment. Pseudo numbers in FIG. 8A illustrate an instance when elements in a target set share one or more segments. For example, Element A and Element B in the target set share both Segment 1 and Segment 2. When considering local median coverage for Element A and Element B, Segment 1 and Segment 2 will be taken into account in both elements. It should be appreciated that it is possible that not all elements share a segment with another element in the target set. and it is possible that no element has a same segment with another element in the target set. FIG. 8A should not be appreciated as a limitation in any purpose.

A local median coverage for each element in a target set in a sample and a global median coverage for all segments in the sample should be determined before performing a first normalization. Only segments covered by an element in the target set will be considered in determining the local median coverage for the element. For example, in FIG. 8A, when determining the local median coverage for Element A, only Segments 1-3 are considered. To determine the local median coverage for Element A, median coverages of Segments 1-3 are arranged from the smallest to the largest (1054 for Segment 3, 1064 for Segment 1, and 1099 for Segment 2) and the middle number (1064) is the local median coverage for Element A. It should be appreciated that the sorting of median coverages and the selecting of a middle number can be done temporarily and there is no need to store sorting information. It should be also appreciated that the arranging of median coverages can be from the largest to the smallest. If there is an even number of segments in the element, the median can be either (i) one of the two numbers in the middle, or (ii) a mathematical mean of the two numbers in the middle. The local median coverage for Element B in FIG. 9A shows the latter determination of the median.

The global median coverage for all segments in a sample can be determined in a similar way as the determination of a local median coverage, except that in the determination of the global median coverage, all segments in the same are sorted to provide a middle number. For example, in FIG. 9A, entries in the last row except the last entry show the median coverages for all the segments in Sample 1. After sorting all the median coverages, a median (1060) can be found and be assigned to the global median coverage for all segments in Sample 1. In many instances, each segment in the sample is covered by at least one element. It should be appreciated that segments need not to be covered by any element and a determination of a global median coverage can either count the uncovered segments or exclude these segments. It should also be appreciated that a global median coverage for all segments is not necessary equal to a median for all elements.

The first normalization is performed based on the local median coverage for each element in a target set in a sample and a global median coverage for all segments in the sample. A first normalized coverage is determined for each element in a target set in a sample. As shown in FIG. 9B, the first normalized coverage for Element A equals the local median coverage for Element A (1064) divided by the global median coverage (1060). The way to determine a local median coverage can be applied to each element in each target set in each sample.

A first normalization was performed within each sample, while a second normalization was performed across samples. For example, in FIG. 9C, a second normalization was performed for Element B across Sample 1 to Sample Z. A second normalized coverage for Element B in each sample was determined based on a first normalized coverage for Element B in each sample and a mean coverage. The mean coverage is a mathematical average of all first normalized coverage for Element B. One method to determine the second normalized coverage for Element B in a sample is to divide the first normalized coverage for Element B in the sample by the mean coverage, as shown in the third column in FIG. 9C. The last column in FIG. 9C shows the second normalized coverage for element B in Samples 1-Z. A CNV detection disclosed in this application is based on the second normalized coverage.

In some instances, an existence of an outlier may affect the accuracy of the disclosed method. An outlier exclusion may be performed before determining a mean coverage. For example, in FIG. 9D, circles mark an outlier in the first coverage number of Element B. An outlier determination rule may be predetermined, and the rule may be Tukey's Fences or the like. If an exclusion applies, then a mean coverage is determined without taking the outlier into account. The right table in FIG. 9D shows a new mean coverage for Element B under an outlier exclusion rule. The following steps to determine a second normalized coverage for Element B in each sample are the same with the example shown in FIG. 9C, and the second normalized coverage provide information to perform a next step of CNV detection.

IV.B. An Experiment with 1911 Samples

Real-world experiments were performed with 1911 samples in 23 flowcells. The experiments used Tukey's Fences as the exclusion rule and combine the second normalized coverage with its p-value to determine whether a CNV exist at the corresponding location of an element. In the experiments, three chromosomal CNVs were detected using the disclosed method, of which occurrence is consistent with literature in the art. At the same time, 41 gene CNVs were detected as well as 113 exons relating to 18

Figure 10:
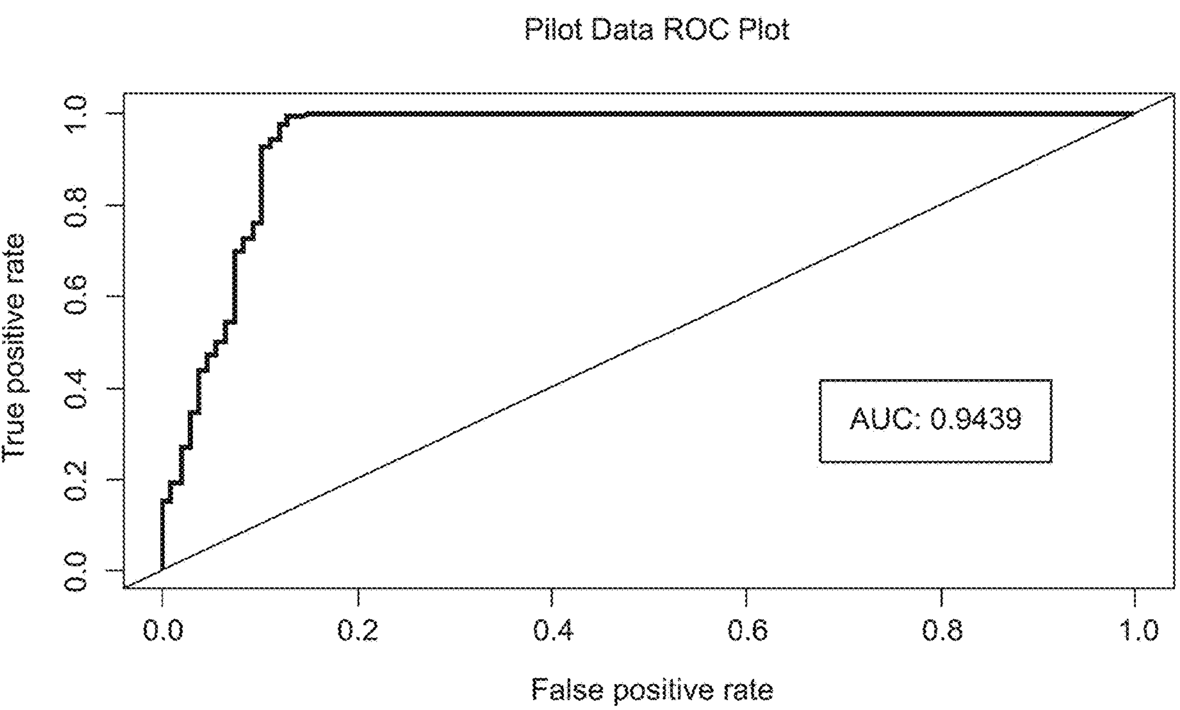
FIG. 10 shows a receiver operating characteristic (ROC) curve depicting an experimental result with 1911 samples according to various embodiments.

CNVs. Examining the overall performance of the experiments using the disclosed method, a receiver operating characteristic (ROC) curve shows a true positive rate (TPR) of 0.974 and a false positive rate (FPR) of 0.12. The discriminatory power of the model using the disclosed method thus is 0.944, as shown in FIG. 10.

Figure 11A:
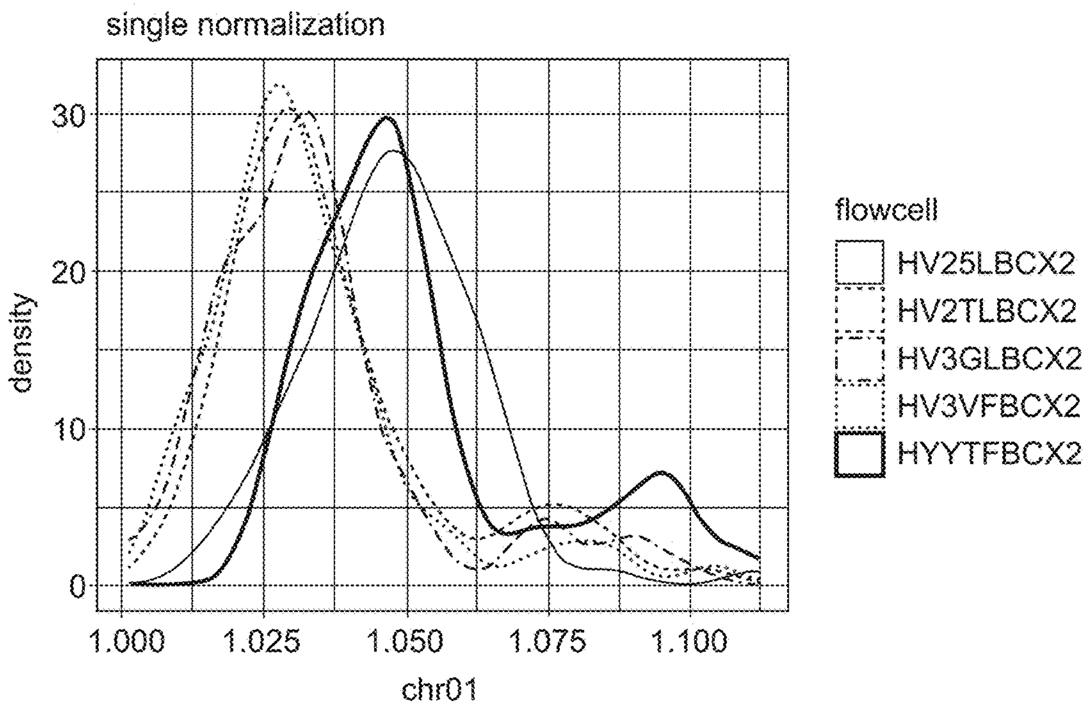
FIG. 11A shows an experimental distribution of element median coverage ratios for Chromosome 1 in the 1911 samples according to various embodiments.
Figure 11B:
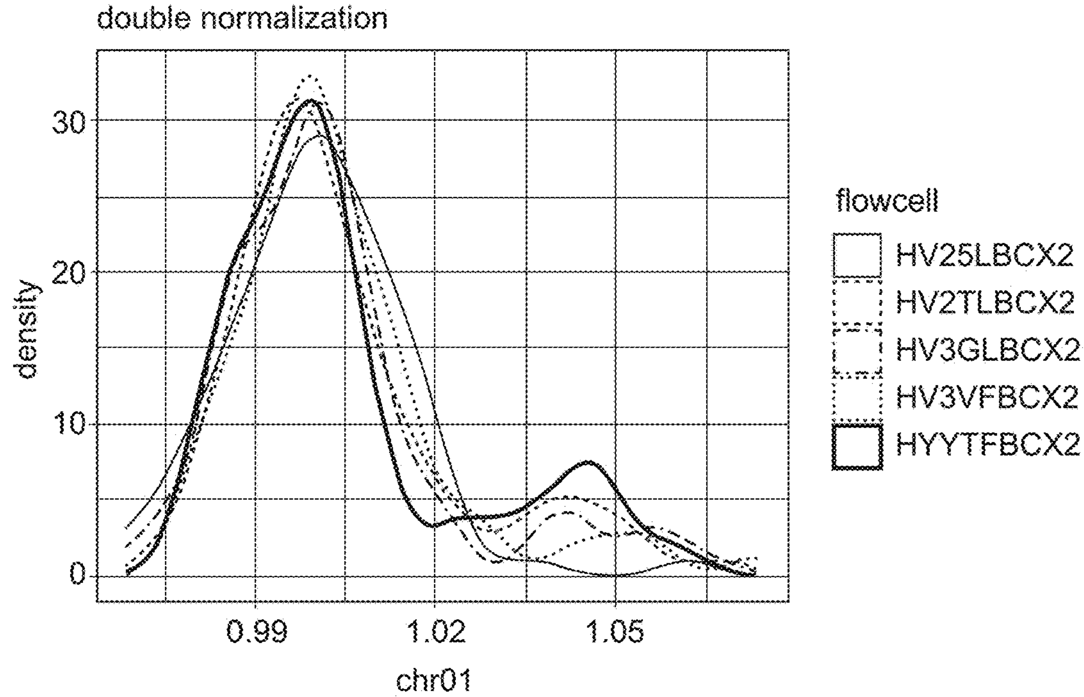
FIG. 11B shows an experimental distribution of copy numbers for Chromosome in the 1911 samples according to various embodiments.

FIGS. 11A and 11B show a distribution of first normalization coverage for Chromosome 1 and a distribution of second normalized coverage for Chromosome 1. It is illustrated from FIG. 11A that the first normalization adjusts data collecting through different flowcells to a similar scale, but different flowcells correspond to a difference center of the distribution. The second normalization provides a re-center of the adjusted data as shown in FIG. 11B. After the second normalization, each distribution corresponding to different flowcells has roughly the same center and the same shape of distribution. The double normalization provides standardized data to perform a CNV detection.

FIGS. 12A and 12B illustrate data distribution in boxplots. FIG. 12A shows boxplots of median coverages for segments covered by different chromosomes (Chromosomes 1-22 and Chromosome X). It is illustrated that the "raw" coverage number distributions for different chromosomes are not similar, and each center of the distributions locates at different positions. FIG. 12B shows distributions of the second normalized coverage across chromosomes in two different gender groups. The upper figure shows the distributions corresponding to female subjects and the lower figure shows the distributions corresponding to male subjects. The center of data for each chromosome in both figures is roughly 1.0, with an exception that the center for Chromosome X in male subjects is roughly 0.5. This exception also proves that normal males have only one Chromosome X, in comparison of females having two. FIG. 12B also suggests that if samples from male subjects and from female subjects are analyzed together to detect CNVs on Chromosome X, an adjustment to the "raw" coverage numbers for segments on Chromosome X from male subject or an adjustment to the first normalized coverage for elements on Chromosome X from male subject should be performed before performing a second normalization. In most instances, the adjustment is to double the coverage numbers or to double the first normalized coverage. Once the adjustment to the "raw" coverages for elements on Chromosome X is done, the normal male and female subjects will both have the copy numbers centered around 1.0 (the expected copy number), and any significant deviations would indicate likely abnormal copy numbers in the sample.

Figure 13:
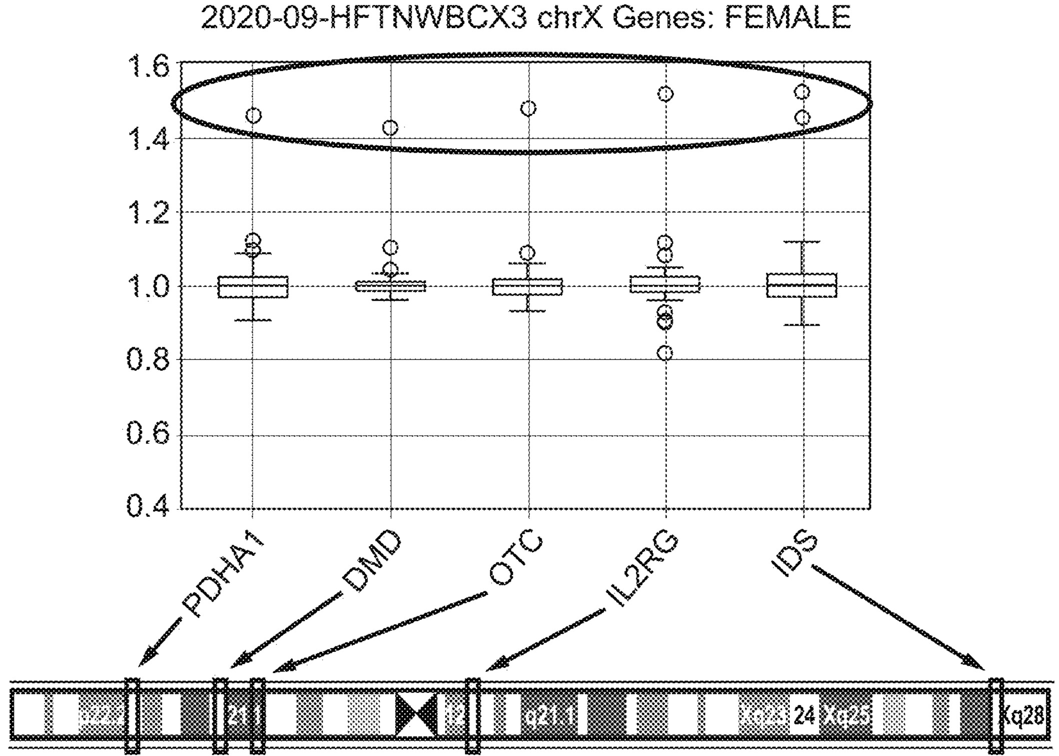
FIG. 13 shows a CNV detection result on Chromosome X from female subjects according to various embodiments.

FIG. 13 shows a CNV detection result on Chromosome X from a female subject. A circle marks abnormal second normalized coverage for every gene on Chromosome X from a female subject. The abnormal second normalized coverage suggests a CNV on the whole Chromosome X. The values of the second normalized coverage are around 1.5 comparing to a "normal" second normalized coverage of value 1.0, which suggests the female subject has an extra sex chromosome, consistent with the finding of an independent method. This CNV detection information can be further used in disease diagnosis, administration of a treatment to the female subject, or the like.

Figure 14:
FIG. 14 shows a CNV detection of a partial chromosomal loss on Chromosome X from female subjects according to various embodiments.

FIG. 14 shows a CNV detection of a partial chromosomal loss on Chromosome X from female subjects. A circle marks abnormal second normalized coverage for three genes (PDHA1, DMD and, OTC) on the p-arm of Chromosome X from a female subject, while its second normalized coverage for the other two genes (IL2RG and IDS) on the q-arm of Chromosome X are not abnormal. The abnormal second normalized coverage suggests a CNV on partial Chromosome X. The values of the abnormal second normalized coverage are around 0.5 comparing to a "normal" second normalized coverage of value 1.0 for the three genes on the p-arm of Chromosome X, which suggests the female subject has partial or complete loss of the p-arm of her Chromosome X, while the q-arm is intact or mostly intact with both copies, consistent with the finding of an independent method. This CNV detection information can also be used in disease diagnosis, administration of a treatment to the female subject, or the like.

Figure 15:
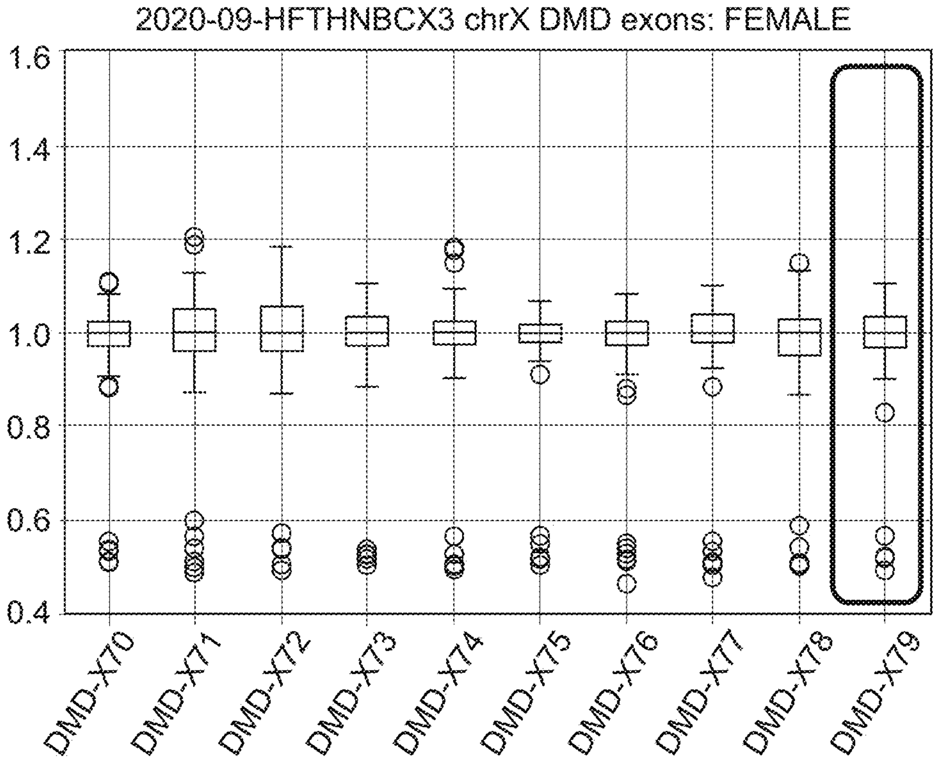
FIG. 15 shows the CNV detection techniques are also compatible to perform small-exon/region CNV detection according to various embodiments.

FIG. 15 shows that the detection method is also compatible to perform exon-scale CNV detection. Points having a value around 0.5 suggest the corresponding exons are missing one copy. The rectangular marks a distribution of the second normalized coverage of DMD-X79 exon, the base pair length of which is only 52. This experiment result also suggests the exon CNV detection using the disclosed method is not affected by small region size.

Figure 16A:
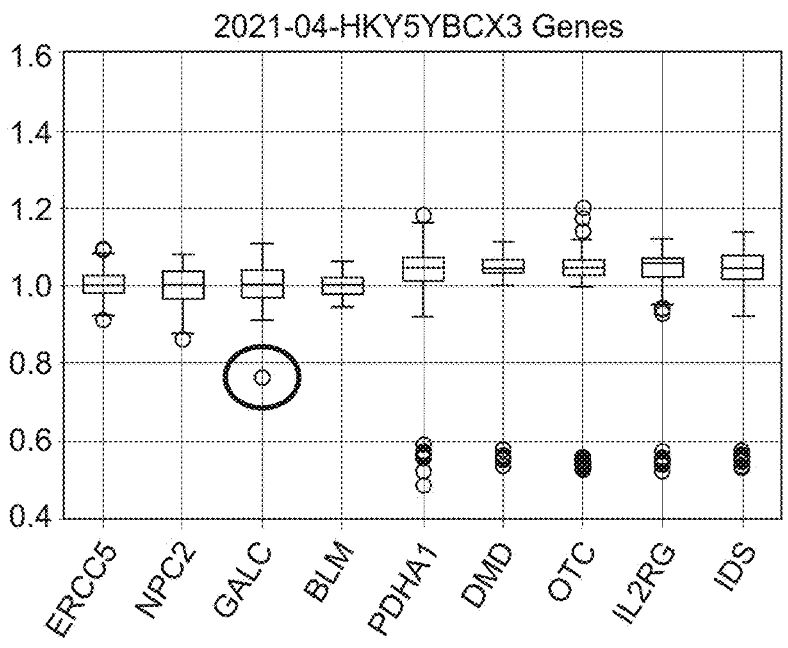
FIG. 16A shows a detection result suggesting a possible partial GALC deletion according to various embodiments.
Figure 16B:
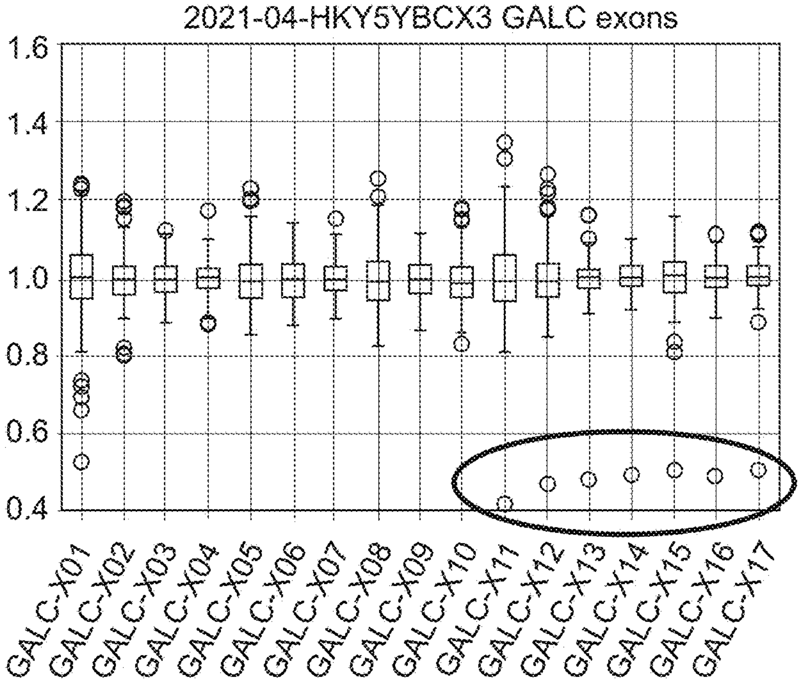
FIG. 16B shows a detection result suggesting a GALC exon deletion according to various embodiments.

A further experiment shows that CNV detection can be performed in combination of gene-level and exon-level. The circle in FIG. 16A marks a critical second normalized coverage for Gene GALC. The value of the circled second normalized coverage is around 0.75, which is not close enough to be an absolute abnormal value, but could suggest maybe partial gene is missing. A further "zoom-in" into the exon-level CNV detection shows that Exons 11-17 of GALC are missing one copy, as illustrated by FIG.16B. The breakpoint between exon 10 and 11 has been confirmed by Sanger sequencing. The results suggest that CNV detection can be performed in combination of neighboring exons or even bins to provide a streamline CNV reporting.

IV.C. An Experiment with 10000 Samples

Figure 17A:
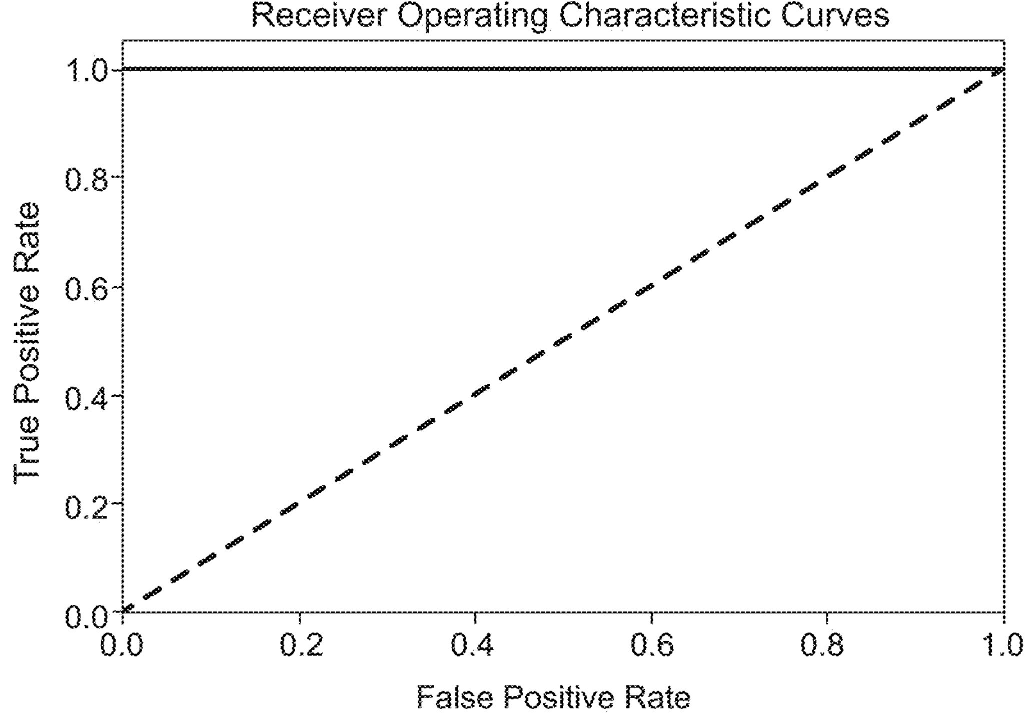
FIG. 17A shows performance with a machine learning model according to various embodiments.

Real-world experiments were performed with about 10000 samples in about 110 flowcells. The experiments used machine learning approaches including use of a random forest model developed based on historical sample data including raw coverage values, the copy number for elements, the normal profile of the elements, p-values, z-scores, and GC %. Examining the overall performance of the experiments using the disclosed machine learning approaches, ROC curve and the area under the curve (AUC) (indicative of model discriminatory power) show a sensitivity or true positive rate (TPR) of 0.97 and a specificity of 0.995 (and a false positive rate of 0.005). The discriminatory power of the model using the disclosed method thus is 0.9999, as shown in FIG. 17A. Moreover, FIG. 17B shows that the machine learning model was able to correctly identify a presence of a CNV (deletions) in a number of instances where the rule-based approaches had failed to identify the presence of the CNV.

V. ADDITIONAL CONSIDERATIONS

Although specific examples have been described, various modifications, alterations, alternative constructions, and equivalents are possible. Examples are not restricted to operation within certain specific data processing environments but are free to operate within a plurality of data processing environments. Additionally, although certain examples have been described using a particular series of transactions and steps, it should be apparent to those skilled in the art that this is not intended to be limiting. Although some flowcharts describe operations as a sequential process, many of the operations may be performed in parallel or concurrently. In addition, the order of the operations may be rearranged. A process may have additional steps not included in the figure. Various features and aspects of the above-described examples may be used individually or jointly.

Further, while certain examples have been described using a particular combination of hardware and software, it should be recognized that other combinations of hardware and software are also possible. Certain examples may be implemented only in hardware, or only in software, or using combinations thereof. The various processes described herein may be implemented on the same processor or different processors in any combination.

Where devices, systems, components or modules are described as being configured to perform certain operations or functions, such configuration may be accomplished, for example, by designing electronic circuits to perform the operation, by programming programmable electronic circuits (such as microprocessors) to perform the operation such as by executing computer instructions or code, or processors or cores programmed to execute code or instructions stored on a non-transitory memory medium, or any combination thereof. Processes may communicate using a variety of techniques including but not limited to conventional techniques for inter-process communications, and different pairs of processes may use different techniques, or the same pair of processes may use different techniques at different times.

Specific details are given in this disclosure to provide a thorough understanding of the examples. However, examples may be practiced without these specific details. For example, well-known circuits, processes, algorithms, structures, and techniques have been shown without unnecessary detail in order to avoid obscuring the examples. This description provides example examples only, and is not intended to limit the scope, applicability, or configuration of other examples. Rather, the preceding description of the examples will provide those skilled in the art with an enabling description for implementing various examples. Various changes may be made in the function and arrangement of elements.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific examples have been described, these are not intended to be limiting. Various modifications and equivalents are within the scope of the following claims.

In the foregoing specification, aspects of the disclosure are described with reference to specific examples thereof, but those skilled in the art will recognize that the disclosure is not limited thereto. Various features and aspects of the above-described disclosure may be used individually or jointly. Further, examples may be utilized in any number of environments and applications beyond those described herein without departing from the broader spirit and scope of the specification. The specification and drawings are, accordingly, to be regarded as illustrative rather than restrictive.

In the foregoing description, for the purposes of illustration, methods were described in a particular order. It should be appreciated that in alternate examples, the methods may be performed in a different order than that described. It should also be appreciated that the methods described above may be performed by hardware components or may be embodied in sequences of machine-executable instructions, which may be used to cause a machine, such as a general-purpose or special-purpose processor or logic circuits programmed with the instructions to perform the methods. These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

Where components are described as being configured to perform certain operations, such configuration may be accomplished, for example, by designing electronic circuits or other hardware to perform the operation, by programming programmable electronic circuits (e.g., microprocessors, or other suitable electronic circuits) to perform the operation, or any combination thereof.

While illustrative examples of the application have been described in detail herein, it is to be understood that the inventive concepts may be otherwise variously embodied and employed, and that the appended claims are intended to be construed to include such variations, except as limited by the prior art.

What is claimed is:

1. A computer-implemented method for detecting a presence or absence of copy number variation in a target sample, comprising:

sequencing, by a massively parallel sequencer, nucleic acids from a plurality of samples as a batch run to generate sequencing data for the plurality of samples, wherein the plurality of samples includes the target sample, and wherein one or more of the plurality of samples are from different subjects;

obtaining, by a computing device, the sequencing data for the plurality of samples;

generating modified sequencing data for the plurality of samples by applying one or more mapping rules to the sequencing data, wherein the modified sequencing data comprises, for each sample of the plurality of samples: (i) a statistical coverage for each segment in the sample, and (ii) a global statistical coverage for all segments in the sample;

determining, by the computing device, for each sample of the plurality of samples, a first normalized coverage for each segment in the sample, wherein the determining the first normalized coverage for each segment in the sample comprises determining a segment statistical coverage ratio for the segment in the sample based on the statistical coverage for the segment and the global statistical coverage for all segments in the sample;

determining, by the computing device, for each sample of the plurality of samples, a second normalized coverage for each segment in the sample, wherein the determining the second normalized coverage for each segment in the sample comprises determining a copy number for the segment in the sample based on the first normalized coverage for the segment in the sample and a measure of central tendency of the first normalized coverage for the segment in all of the plurality of samples;

training, by the computing device, a machine learning model using a training set of training samples to classify the presence or absence of copy number variation, wherein the training set comprises a set of copy numbers corresponding to the training samples and corresponding ground truth labels for the presence or absence of copy number variation, wherein the training comprises:

inputting the set of copy numbers and the ground truth labels into the machine learning model, adjusting parameters of the machine learning model to minimize a loss function indicative of classification error, and validating the machine learning model using a validation set distinct from the training set;

inputting, by the computing device, the copy number for each segment in a target set in the target sample into the trained machine learning model, wherein the target set comprises one or more segments from all of the segments in the target sample; and outputting, by the computing device, a classification for the presence or absence of the copy number variation for each segment in the target set in the target sample according to the classification by the trained machine learning model.

2. The computer-implemented method of claim 1, wherein the generating the modified sequencing data for the plurality of samples comprises:

mapping sequence reads in the sequencing data to a reference genome;

counting the sequence reads mapped to genomic portions of the reference genome, wherein the counting generates a quantification of the sequence reads mapped to the genomic portions of the reference genome for each sample;

determining a base coverage for each reference base within each segment of each sample based on the quantification of the sequence reads mapped to each reference base within each segment;

determining the statistical coverage for each segment in each sample; and determining the global statistical coverage for all segments in each sample.

3. The computer-implemented method of claim 1, wherein the sequencing the nucleic acids generates hundreds of thousands to hundreds of millions of sequence reads for each sample.

4. The computer-implemented method of claim 1, wherein the statistical coverage for each segment in a sample is a median coverage for each segment in the sample, the global statistical coverage for all segments in the sample is a global median coverage for all segments in the sample, the measure of central tendency of the first normalized coverage for the segment in all of the plurality of samples is a mean of the first normalized coverage for the segment in all of the plurality of samples, and the determining the segment statistical coverage ratio for the segment in the sample comprises dividing the median coverage for the segment by the global median coverage for all segments in the sample.

5. The computer-implemented method of claim 1, wherein the determining the second normalized coverage for each segment in each of the samples further comprises removing outliers from the statistical coverage for the segment in each sample of the plurality of samples before determining the segment statistical coverage ratio for the segment in each sample of the plurality of samples, and calculating a mean of the segment statistical coverage ratio for the segment in remaining samples of the plurality of samples.

6. The computer-implemented method of claim 1, further comprising (i) removing one or more statistical coverage for one or more segments on a sex chromosome in one or more samples from the obtained sequencing data, (ii) removing one or more statistical coverage for one or more segments on Chromosome X in one or more samples associated with male subjects from the obtained sequencing data, (iii) doubling one or more statistical coverage for one or more segments on Chromosome X in one or more samples associated with male subjects in the obtained sequencing data, or (iv) any combination thereof.

7. The computer-implemented method of claim 1, further comprising:

determining, by the computing device, a first normalized coverage for an element in each sample of the plurality of samples, wherein the element is (i) a chromosome, (ii) a portion of the chromosome, (iii) a gene, (iv) an exon, (v) an intron, or (vi) a predetermined genomic part or region of interest, wherein the segment is a part of the element, and wherein the determining the first normalized coverage for the element in each sample comprises:

determining a local statistical coverage for the element in the sample; and determining an element statistical coverage ratio for the element in the sample based on the local statistical coverage for the element and the global statistical coverage for all segments in the sample;

determining, by the computing device, a second normalized coverage for the element in each sample of the plurality of samples, the determining the second normalized coverage for the element in each sample comprises determining a copy number for the element in the sample based on the first normalized coverage for the element in the sample and a measure of central tendency of the first normalized coverage for the element in all of the plurality of samples;

inputting, by the computing device, the copy number for the element in the target sample into the trained machine learning model; and outputting, by the computing device, a classification for the presence or absence of the copy number variation for the element in the target sample according to the classification by the trained machine learning model.

8. The computer-implemented method of claim 7, wherein the determining the second normalized coverage for the element further comprises removing outliers from the element statistical coverage ratio for the element in all of the plurality of samples before determining the measure of central tendency of the first normalized coverage for the element in all of the plurality of samples, and calculating a mean of the element statistical coverage ratio for the element in remaining samples of the plurality of samples.

9. The computer-implemented method of claim 8, wherein the removing the outliers comprises:

calculating an interquartile range based on the element statistical coverage ratio for the element in all of the plurality of samples;

determining an upper limit and a lower limit relating to the interquartile range; and removing any element statistical coverage ratio for the element where a value of the element statistical coverage ratio is greater than the upper limit or less than the lower limit.

10. The computer-implemented method of claim 1, further comprising determining, by the computing device, whether the copy number for each segment in the target set in the target sample is within or outside of a predetermined interval based on the classification, wherein the outputting comprises reporting each segment in the target set in the target sample that has a copy number outside the predetermined interval as having the copy number variation, and reporting each segment in the target set in the target sample that has a copy number within the predetermined interval as being normal or not having the copy number variation.

11. The computer-implemented method of claim 7, further comprising determining, by the computing device, whether the copy number for the element in the target sample is within or outside of a predetermined interval based on the classification, wherein the outputting comprises reporting the element as having the copy number variation when the element in the target sample has a copy number outside the predetermined interval, or reporting the element as being normal or not having the copy number variation when the element in the target sample has a copy number within the predetermined interval.

12. The computer-implemented method of claim 11, further comprising:

calculating a statistical measure for each segment in the target set and/or the element, wherein the calculation of the statistical measure is based on a normal profile comprising the copy number for each segment in the target set and/or the element in all samples; and comparing the statistical measure with a predetermined upper-threshold or with a predetermined lower-threshold set for segments and/or the element, wherein each segment in the target in the target sample that has a copy number within the predetermined interval is only reported as having the copy number variation when the statistical measure of the segment in the target set is greater than the predetermined upper-threshold or less than the predetermined lower-threshold based on the comparing; and/or wherein the element in the target sample that has a copy number within the predetermined interval is only reported as having the copy number variation when the statistical measure of the element is greater than the predetermined upper-threshold or less than the predetermined lower-threshold based on the comparing.

13. The computer-implemented method of claim 12, wherein the statistical measure comprises (i) a z-score, (ii) a p-value, or (iii) a coefficient of variation.

14. The computer-implemented method of claim 1, further comprising determining a diagnosis of a subject associated with the target sample, wherein the diagnosis is determined based on the classification for the presence or absence of the copy number variation for each segment in the target set in the target sample.

15. The computer-implemented method of claim 14, further comprising administering a treatment to the subject based on (i) the classification for the presence or absence of the copy number variation for each segment in the target set in the target sample, and/or (ii) the diagnosis of the subject.

16. A computer-implemented method for detecting a presence or absence of copy number variation in a target sample, comprising:

sequencing, by a massively parallel sequencer, nucleic acids from a plurality of samples as a batch run to generate sequencing data for the plurality of samples wherein the plurality of samples includes the target sample, and wherein one or more of the samples are from different subjects;

obtaining, by a computing device, the sequencing data for the plurality of samples;

generating modified sequencing data for the plurality of samples by applying one or more mapping rules to the sequencing data, wherein the modified sequencing data comprises, for each sample of the plurality of samples: (i) a median coverage for each segment in the sample, and (ii) a global median coverage for all segments in the sample;

determining, by the computing device for each sample of the plurality of samples, a first normalized coverage for an element in the sample, wherein the element comprises two or more segments, and wherein the determining the first normalized coverage for the element comprises:

determining a local median coverage for the element in the sample; and determining an element median coverage ratio for the element in the sample based on the local median coverage for the element and the global median coverage for all segments in the sample;

determining, by the computing device for each sample of the plurality of samples, a second normalized coverage for the element in the sample, wherein the determining the second normalized coverage for the element comprises determining a copy number for the element in the sample based on the first normalized coverage for the element in the sample and a mean of the first normalized coverage for the element in all of the plurality of samples;

training, by the computing device, a machine learning model using a training set of training samples to classify the presence or absence of copy number variation, wherein the training set comprises a set of copy numbers corresponding to the training samples and corresponding ground truth labels for the presence or absence of copy number variation, wherein the training comprises:

inputting the set of copy numbers and the ground truth labels into the machine learning model, adjusting parameters of the machine learning model to minimize a loss function indicative of classification error, and validating the machine learning model using a validation set distinct from the training set;

inputting, by the computing device, the copy number for the element in the target sample into the trained machine learning model; and outputting, by the computing device, a classification for the presence or absence of the copy number variation for the element in the target sample according to the classification by the trained machine learning model.

17. A system comprising:

a massively parallel sequencer, wherein the massively parallel sequencer sequences nucleic acids obtained from a plurality of samples as a batch run to generate sequencing data for the plurality of samples, wherein the plurality of samples includes a target sample, and wherein one or more of the plurality of samples are from different subjects;

a processor; and a non-transitory memory comprising computer program instructions that when executed by the processor, cause the processor to perform obtaining the sequencing data for the plurality of samples generated by the massively parallel sequencer;

generating modified sequencing data for the plurality of samples by applying one or more mapping rules to the sequencing data, wherein the modified sequencing data comprises, for each sample of the plurality of samples: (i) a median coverage for each segment in the sample, and (ii) a global median coverage for all segments in the sample;

determining, for each sample of the plurality of samples, a first normalized coverage for an element in the sample, wherein the element comprises two or more segments, and wherein the determining the first normalized coverage for the element comprises:

determining a local median coverage for the element in the sample; and determining an element median coverage ratio for the element in the sample based on the local median coverage for the element and the global median coverage for all segments in the sample;

determining, for each sample of the plurality of samples, a second normalized coverage for the element in the sample, wherein the determining the second normalized coverage for the element comprises determining a copy number for the element in the sample based on the first normalized coverage for the element in the sample and a mean of the first normalized coverage for the element in all of the plurality of samples;

training a machine learning model using a training set of training samples to classify a presence or absence of copy number variation, wherein the training set comprises a set of copy numbers corresponding to the training samples and corresponding ground truth labels for the presence or absence of copy number variation, wherein the training comprises:

inputting the set of copy numbers and the ground truth labels into the machine learning model, adjusting parameters of the machine learning model to minimize a loss function indicative of classification error, and validating the machine learning model using a validation set distinct from the training set;

inputting the copy number for the element in the target sample into the trained machine learning model; and outputting a classification for a presence or absence of a copy number variation for the element in the target sample according to the classification by the trained machine learning model.

18. The computer-implemented method of claim 16, further comprising determining, by the computing device, whether the copy number for the element in the target sample is within or outside of a predetermined interval based on the classification, wherein the outputting comprises reporting the element in the target sample that has a copy number outside the predetermined interval as having the copy number variation, and reporting the element in the target sample that has a copy number within the predetermined interval as being normal or not having the copy number variation.

19. The system of claim 17, wherein the processor is further caused to perform determining whether the copy number for the element in the target sample is within or outside of a predetermined interval based on the classification, wherein the outputting comprises reporting the element in the target sample that has a copy number outside the predetermined interval as having the copy number variation, and reporting the element in the target sample that has a copy number within the predetermined interval as being normal or not having the copy number variation.

* * * * *